(12) United States Patent
Aoyama et al.

(10) Patent No.: US 10,021,880 B2
(45) Date of Patent: Jul. 17, 2018

(54) DIARYLIMIDAZOLE COMPOUND AND HARMFUL ORGANISM CONTROL AGENT

(71) Applicant: Nippon Soda Co., Ltd., Chiyoda-ku, Tokyo (JP)

(72) Inventors: Hikaru Aoyama, Kanagawa (JP); Maki Matsui, Kanagawa (JP); Takao Iwasa, Kanagawa (JP); Kazushige Fujii, Kanagawa (JP); Tomomi Kobayashi, Kanagawa (JP); Keita Sakanishi, Kanagawa (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 15/501,921

(22) PCT Filed: Aug. 11, 2015

(86) PCT No.: PCT/JP2015/072762
§ 371 (c)(1),
(2) Date: Feb. 6, 2017

(87) PCT Pub. No.: WO2016/024587
PCT Pub. Date: Feb. 18, 2016

(65) Prior Publication Data
US 2017/0223958 A1 Aug. 10, 2017

(30) Foreign Application Priority Data
Aug. 13, 2014 (JP) .................................. 2014-165034

(51) Int. Cl.
| | | |
|---|---|---|
| C07D 233/64 | (2006.01) | |
| C07D 233/90 | (2006.01) | |
| C07D 233/92 | (2006.01) | |
| A01N 43/50 | (2006.01) | |
| C07D 401/04 | (2006.01) | |
| C07D 403/04 | (2006.01) | |
| A01N 43/56 | (2006.01) | |
| C07D 401/14 | (2006.01) | |
| A01N 43/54 | (2006.01) | |
| C07D 405/04 | (2006.01) | |
| A01N 43/58 | (2006.01) | |
| C07D 409/04 | (2006.01) | |
| C07D 417/14 | (2006.01) | |
| A01N 43/74 | (2006.01) | |

(52) U.S. Cl.
CPC ............. *A01N 43/50* (2013.01); *A01N 43/54* (2013.01); *A01N 43/56* (2013.01); *A01N 43/58* (2013.01); *A01N 43/74* (2013.01); *C07D 233/64* (2013.01); *C07D 401/04* (2013.01); *C07D 401/14* (2013.01); *C07D 403/04* (2013.01); *C07D 405/04* (2013.01); *C07D 409/04* (2013.01); *C07D 417/14* (2013.01)

(58) Field of Classification Search
CPC .. C07D 403/04; C07D 233/64; C07D 233/90; C07D 233/92
USPC ........................................ 548/312.4; 514/397
See application file for complete search history.

(56) References Cited

U.S. PATENT DOCUMENTS

| | | |
|---|---|---|
| 4,822,805 A | 4/1989 | Takasugi et al. |
| 6,255,327 B1 | 7/2001 | Brenner et al. |
| 2005/0187218 A1 | 8/2005 | Marinier et al. |

FOREIGN PATENT DOCUMENTS

| | | |
|---|---|---|
| CN | 103833734 A | 6/2014 |
| EP | 0712847 A1 | 5/1996 |
| JP | 63-054369 A | 3/1988 |
| JP | 01-258670 A | 10/1989 |
| JP | 09-506876 A | 7/1997 |
| JP | 2000-273088 A | 10/2000 |
| JP | 2001-163861 A | 6/2001 |
| JP | 2002-512235 A | 4/2002 |
| JP | 2005-528368 A | 9/2005 |

(Continued)

OTHER PUBLICATIONS

International Search Report dated Nov. 17, 2015, in PCT/JP2015/072762.

(Continued)

*Primary Examiner* — Patricia L Morris
(74) *Attorney, Agent, or Firm* — Foley & Lardner LLP

(57) ABSTRACT

The present invention provides a compound represented by formula (I) or salt thereof (in the formula, $A^1$ and $A^2$ each independently represents a nitrogen atom or the like, $B^1$, $B^2$, $B^3$ and $B^4$ each independently represents a carbon atom or nitrogen atom, $X^1$ represents an unsubstituted or substituted C1-6 alkyl group or the like, n represents a number of $X^1$ and represents an integer of 0-4, $R^1$ represents a halogeno group or the like, $R^2$ represents an unsubstituted or substituted C1-6 alkyl group or the like, m represents a number of the oxide group bonding with the nitrogen atom which does not bond with $R^2$ on the imidazole ring, and represents 0 or 1, $R^3$ represents a hydrogen atom or the like, Ar represents an unsubstituted or substituted C6-10 aryl group.

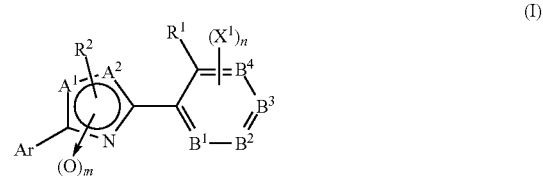

(I)

2 Claims, No Drawings

(56) References Cited

FOREIGN PATENT DOCUMENTS

| JP | 2007-508345 A | 4/2007 |
|---|---|---|
| JP | 2008-528649 A | 7/2008 |
| JP | 2011-510928 A | 4/2011 |
| JP | 2012-041325 A | 3/2012 |
| WO | WO 95/04724 A1 | 2/1995 |
| WO | WO 98/27108 A2 | 6/1998 |
| WO | WO 03/082829 A1 | 10/2003 |
| WO | WO 2005/040153 A1 | 5/2005 |
| WO | WO 2006/082002 A1 | 8/2006 |
| WO | WO 2008/084218 A1 | 7/2008 |
| WO | WO 2008/129981 A1 | 10/2008 |
| WO | WO 2009/094445 A2 | 7/2009 |
| WO | WO 2010/065579 A2 | 6/2010 |
| WO | WO 2012/025460 A1 | 3/2012 |
| WO | WO 2013/173218 A1 | 11/2013 |
| WO | WO 2015/038872 A1 | 3/2015 |
| WO | WO 2015/144895 A1 | 10/2015 |

OTHER PUBLICATIONS

Allan et al., "Imidazoles, Ill. Pesticidal Screening of Some Substituted 1-Hydroxyimidazoles," Pesticide Science, 1972, 3:153-159.
Supplementary European Search Report dated Jan. 5, 2018, in EP 15831879.0.

DIARYLIMIDAZOLE COMPOUND AND HARMFUL ORGANISM CONTROL AGENT

TECHNICAL FIELD

The present invention relates to a diarylimidazole compound and a harmful organism control agent. More specifically, the present invention relates to a diarylimidazole compound and a harmful organism control agent containing the diarylimidazole compound as an active ingredient. The diarylimidazole compound has a superior acaricidal and/or insecticidal activity, superior safety, and can be advantageously and industrially synthesized.

CROSS-REFERENCE TO RELATED APPLICATIONS

The present application is the U.S. National Stage application of PCT/JP2015/072762, filed Aug. 11, 2015, which claims priority from Japanese Patent Application No. 2014-165034, filed Aug. 13, 2014, the content of which is incorporated herein by reference.

BACKGROUND ART

Various compounds having an acaricidal and/or insecticidal activity have been suggested. In order to practically use these compounds as an agrochemical, the compounds are required to have a sufficient efficacy, and also to have other properties such as being hard to cause drug-resistance, preventing phytotoxicity against the plants and soil contamination, or having a low level of toxicity against livestocks, fishes or the like.

Patent Document 1 discloses a compound represented by formula (A). According to Patent Document 1, this compound has a strong inhibitory activity to the generation of nitrogen monoxide and has an effect for preventing and treating nitrogen monoxide mediated disease.

[Chemical formula 1]

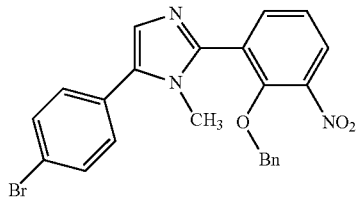

(A)

PRIOR ART LITERATURE

Patent Documents

Patent document 1: WO98/27108A

DISCLOSURE OF INVENTION

Problems to be Solved by the Invention

The objective of the present invention is to provide a diarylimidazole compound or salt thereof as an active ingredient. The diarylimidazole compound has a harmful organism control activity, particularly, a superior acaricidal and/or insecticidal activity, superior safety, and can be synthesized advantageously and industrially. Furthermore, the objective of the present invention is to provide a harmful organism control agent containing the diarylimidazole compound or salt thereof.

Means for Solving the Problems

In order to achieve the above objective, the present inventors conducted extensive studies. As a result, the present inventors discovered that a diarylimidazole compound or salt thereof having a specific structure demonstrates a superior acaricidal and/or insecticidal activity, excellent properties and high safety, and can be used as an active ingredient of harmful organism control agent. Furthermore, the present inventors discovered that the compound can be used as an active ingredient of external parasite control agent. The present invention was achieved on the basis of this perception.

That is, the present invention is as follows:

[1] A compound represented by formula (I) or salt thereof.

[Chemical formula 2]

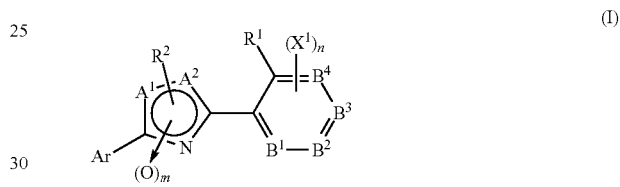

(I)

in formula (I), $A^1$ and $A^2$ each independently represents a nitrogen atom or $CR^3$, provided that $A^1$ and $A^2$ do not simultaneously represent a nitrogen atom or simultaneously represent $CR^3$, $B^1$, $B^2$, $B^3$ and $B^4$ each independently represents a carbon atom or a nitrogen atom, provided that when $B^1$ is a nitrogen atom, $B^2$ and $B^4$ represent a carbon atom and $B^3$ represents a carbon atom or a nitrogen atom, and when $B^1$ is a carbon atom, $B^2$ to $B^4$ represent a carbon atom or a nitrogen atom except that two or more of $B^2$ to $B^4$ simultaneously represent a nitrogen atom, $X^1$ represents an unsubstituted or substituted C1-6 alkyl group, unsubstituted or substituted C2-6 alkenyl group, unsubstituted or substituted C2-6 alkynyl group, hydroxy group, unsubstituted or substituted C1-6 alkoxy group, formyl group, unsubstituted or substituted C1-6 alkyl carbonyl group, unsubstituted or substituted C1-6 alkoxycarbonyl group, unsubstituted or substituted C1-6 alkyl aminocarbonyl group, mercapto group, unsubstituted or substituted C1-6 alkyl thio group, unsubstituted or substituted C1-6 alkyl sulfinyl group, unsubstituted or substituted C1-6 alkyl sulfonyl group, unsubstituted or substituted C3-8 cycloalkyl group, unsubstituted or substituted C6-10 aryl group, unsubstituted or substituted 3-6 membered heterocyclyl group, unsubstituted or substituted amino group, halogen group, cyano group, or nitro group, n represents a chemically acceptable number of $X^1$ and represents an integer of 0 to 4, when n is 2 or more, $X^1$s may be the same or different, and when n is 2 or more, two $X^1$s may bond together to form a ring, $R^1$ represents a halogen group, hydroxy group, cyano group, substituted C1-6 alkyl group, unsubstituted or substituted C1-6 alkoxy group, unsubstituted or substituted C1-6 alkyl thio group, unsubstituted or substituted C1-6 alkyl sulfinyl group, unsubstituted or substituted C1-6 alkyl sulfonyl group, unsubstituted or substituted C1-6 alkyl sulfonyloxy group, C1-6 alkyl aminocarbonyl group, C1-6 alkyl sulfoximino group or a group represented by —S(=O)(=N—R$^a$)—R$^b$, in the formula, R$^a$ represents a hydrogen atom, cyano group, C1-6 alkyl group or unsubstituted or substituted C1-6 alkyl carbonyl group, R$^b$ represents a C1-6 alkyl group, R$^2$ represents an unsubstituted or substituted C1-6 alkyl group, unsubstituted or substituted C2-6 alkenyl group, unsubstituted or substituted C2-6 alkynyl group, unsubstituted or substituted C3-8 cycloalkyl group, hydroxy group, unsubstituted or substituted C1-6 alkoxy group, formyl group, unsubstituted or substituted C1-6 alkyl carbonyl group, unsubstituted or substituted C1-6 alkoxycarbonyl group, or unsubstituted or substituted C1-6 alkyl sulfonyl group. R$^2$ is a substituent bonding with any one of the two nitrogen atoms on the imidazole ring, m represents a number of the oxide group bonding with the nitrogen atom which does not bond with R$^2$ on the imidazole ring, and represents 0 or 1, R$^3$ represents a hydrogen atom, unsubstituted or substituted C1-6 alkyl group, unsubstituted or substituted C6-10 aryl group, halogen group, cyano group or nitro group, Ar represents an unsubstituted or substituted C6-10 aryl group or unsubstituted or substituted 5-10 membered heteroaryl group.

[2] The compound or salt thereof according to [1], wherein formula (I) is formula (II) or formula (II),

[Chemical formula 3]

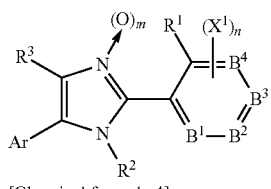

(II)

[Chemical formula 4]

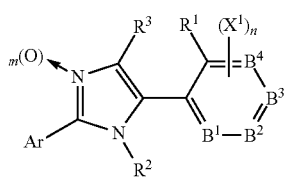

(III)

in formula (II) and formula (III), X$^1$, R$^1$, R$^2$, R$^3$, B$^1$, B$^2$, B$^3$, B$^4$, n, m and Ar are as defined in formula (I).

[3] A harmful organism control agent comprising as an active ingredient at least one selected from the group consisting of the compound and salt thereof defined in [1] or [2].
[4] An insecticide or acaricide comprising as an active ingredient at least one selected from the group consisting of the compound and salt thereof defined in [1] or [2].
[5] An external parasite control agent comprising as an active ingredient at least one selected from the group consisting of the compound and salt thereof defined in [1] or [2].
[6] An internal parasite control agent or expellent comprising as an active ingredient at least one selected from the group consisting of the compound and salt thereof defined in [1] or [2].

Effects of the Invention

The diarylimidazole compound or salt thereof according to the present invention can prevent harmful organisms which are harmful for agricultural crops and cause the problem of hygiene. Particularly, the compound or salt thereof according to the present invention can effectively prevent acari and insecticides. Furthermore, the compound or salt thereof according to the present invention can prevent external parasites and internal parasite which are harmful for humans and animals.

BEST MODE FOR CARRYING OUT THE INVENTION

[Formula (I)]
The diarylimidazole compound of the present invention is a compound represented by formula (I) (thereinafter, may be referred to as compound (I)) or salt of compound (I).

[Chemical formula 5]

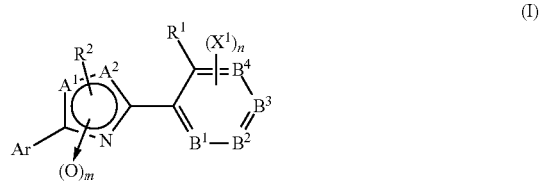

(I)

Firstly, in the present invention, the term "unsubstituted" indicates a group including only a mother nucleus. When a group is referred to as a name of a mother nucleus without "substituted", this refers to "unsubstituted" unless specifically indicated otherwise.

On the other hand, the term "substituted" indicates that at least one of the hydrogen atoms of the mother nucleus is substituted with a substituent having a structure that is the same as the structure of the mother nucleus or different from the structure of the mother nucleus. Thus, a "substituent" is another group bonded with the mother nucleus. There may be one substituent or two or more substituents. Two or more substituents may be the same as or different from each other.

For example, the term "C1-6" or the like indicates that the number of carbon atoms of the mother nucleus is 1 to 6. The number of carbon atoms present in substituents is not included in this number of carbon atoms. For example, a butyl group having an ethoxy group as a substituent thereof is classified as a C2 alkoxy C4 alkyl group.

The "substituent" is not particularly limited as long as it is chemically acceptable and achieves the effects of the present invention.

Examples of the "substituent" are as follows:
a C1-6 alkyl group such as a methyl group, ethyl group, n-propyl group, i-propyl group, n-butyl group, s-butyl group, i-butyl group, t-butyl group, n-pentyl group, n-hexyl group or the like;
a C2-6 alkenyl group such as a vinyl group, 1-propenyl group, 2-propenyl group (allyl group), 1-butenyl group, 2-butenyl group, 3-butenyl group, 1-methyl-2-propenyl group, 2-methyl-2-propenyl group or the like;
a C2-6 alkynyl group such as an ethynyl group, 1-propynyl group, 2-propynyl group, 1-butynyl group, 2-butynyl group, 3-butynyl group, 1-methyl-2-propynyl group or the like;
a C3-8 cycloalkyl group such as a cyclopropyl group, cyclobutyl group, cyclopentyl group, cyclohexyl group, cubanyl group or the like;
a C6-10 aryl group such as a phenyl group, naphthyl group or the like;

a C6-10 aryl C1-6 alkyl group such as a benzyl group, phenethyl group or the like;

a 3-6 membered heterocyclyl group;

a 3-6 membered heterocyclyl C1-6 alkyl group;

a hydroxy group;

a C1-6 alkoxy group such as methoxy group, ethoxy group, n-propoxy group, i-propoxy group, n-butoxy group, s-butoxy group, i-butoxy group, t-butoxy group or the like;

a C2-6 alkenyloxy group such as vinyloxy group, allyloxy group, propenyloxy group, butenyloxy group or the like;

a C2-6 alkynyloxy group such as ethynyloxy group, propargyloxy group or the like;

a C6-10 aryloxy group such as phenoxy group, naphthoxy group or the like;

a C6-10 aryl C1-6 alkoxy group such as benzyloxy group, phenethyloxy group or the like;

a 5-6 membered heteroaryloxy group such as thiazolyloxy group, pyridyloxy group or the like;

a 5-6 membered heteroaryl C1-6 alkyloxy group such as thiazolyl methyloxy group, pyridyl methyloxy group or the like;

a formyl group;

a C1-6 alkyl carbonyl group such as acetyl group, propionyl group or the like;

a formyloxy group;

a C1-6 alkyl carbonyloxy group such as acetyloxy group, propionyloxy group or the like;

a C6-10 aryl carbonyl group such as benzoyl group or the like;

a C1-6 alkoxycarbonyl group such as methoxycarbonyl group, ethoxycarbonyl group, n-propoxycarbonyl group, i-propoxycarbonyl group, n-butoxycarbonyl group, t-butoxycarbonyl group or the like;

a C1-6 alkoxycarbonyloxy group such as methoxycarbonyloxy group, ethoxycarbonyloxy group, n-propoxycarbonyloxy group, i-propoxycarbonyloxy group, n-butoxycarbonyloxy group, t-butoxycarbonyloxy group or the like;

a carboxyl group;

a halogen group such as fluoro group, chloro group, bromo group, iodo group or the like;

a C1-6 haloalkyl group such as chloromethyl group, chloroethyl group, trifluoromethyl group, 1,2-dichloro-n-propyl group, 1-fluoro-n-butyl group, perfluoro-n-pentyl group or the like;

a C2-6 haloalkenyl group such as 2-chloro-1-propenyl group, 2-fluoro-1-butenyl group or the like;

a C2-6 haloalkynyl group such as 4,4-dichloro-1-butynyl group, 4-fluoro-1-pentynyl group, 5-bromo-2-pentynyl group or the like;

a C1-6 haloalkoxy group such as trifluoromethoxy group, 2-chloro-n-propoxy group, 2,3-dichlorobutoxy group or the like;

a C2-6 haloalkenyloxy group such as 2-chloropropenyloxy group, 3-bromobutenyloxy group or the like;

a C1-6 haloalkyl carbonyl group such as chloroacetyl group, trifluoroacetyl group, trichloroacetyl group or the like;

an amino group;

a C1-6 alkyl substituted amino group such as methyl amino group, dimethyl amino group, diethyl amino group or the like;

a C6-10 aryl amino group such as anilino group, naphthyl amino group or the like;

a C6-10 aryl C1-6 alkyl amino group such as benzyl amino group, phenethyl amino group or the like;

a formyl amino group;

a C1-6 alkyl carbonyl amino group such as acetyl amino group, propanoyl amino group, butyryl amino group, i-propyl carbonyl amino group or the like;

a C1-6 alkoxycarbonyl amino group such as methoxycarbonyl amino group, ethoxycarbonyl amino group, n-propoxycarbonyl amino group, i-propoxycarbonyl amino group or the like;

an unsubstituted or substituted aminocarbonyl group such as aminocarbonyl group, dimethyl aminocarbonyl group, phenyl aminocarbonyl group, N-phenyl-N-methyl aminocarbonyl group, N-butyl-N-methyl aminocarbonyl group or the like;

an imino C1-6 alkyl group such as iminomethyl group, (1-imino)ethyl group, (1-imino)-n-propyl group or the like;

an unsubstituted or substituted N-hydroxyimino C1-6 alkyl group such as N-hydroxy-iminomethyl group, (1-(N-hydroxy)-imino)ethyl group, (1-(N-hydroxy)-imino)propyl group, N-methoxy-iminomethyl group, (1-(N-methoxy)-imino)ethyl group or the like;

an aminocarbonyloxy group;

a C1-6 alkyl substituted aminocarbonyloxy group such as ethyl aminocarbonyloxy group, dimethyl aminocarbonyloxy group or the like;

a mercapto group;

a C1-6 alkyl thio group such as methyl thio group, ethyl thio group, n-propyl thio group, i-propyl thio group, n-butyl thio group, i-butyl thio group, s-butyl thio group, t-butyl thio group or the like;

a C1-6 haloalkyl thio group such as trifluoromethyl thio group, 2,2,2-trifluoroethyl thio group or the like;

a C6-10 aryl thio group such as phenyl thio group, naphthyl thio group or the like;

a 5-6 membered heteroaryl thio group such as thiazolyl thio group, pyridyl thio group or the like;

a C1-6 alkyl sulfinyl group such as methyl sulfinyl group, ethyl sulfinyl group, t-butyl sulfinyl group or the like;

a C1-6 haloalkyl sulfinyl group such as trifluoromethyl sulfinyl group, 2,2,2-trifluoroethyl sulfinyl group or the like;

a C6-10 aryl sulfinyl group such as phenyl sulfinyl group or the like; a 5-6 membered heteroaryl sulfinyl group such as thiazolyl sulfinyl group, pyridyl sulfinyl group or the like;

a C1-6 alkyl sulfonyl group such as methyl sulfonyl group, ethyl sulfonyl group, t-butyl sulfonyl group or the like;

a C1-6 haloalkyl sulfonyl group such as trifluoromethyl sulfonyl group, 2,2,2-trifluoroethyl sulfonyl group or the like;

a C6-10 aryl sulfonyl group such as phenyl sulfonyl group or the like; a 5-6 membered heteroaryl sulfonyl group such as thiazolyl sulfonyl group, pyridyl sulfonyl group or the like;

an alkyl sulfonyloxy group such as methyl sulfonyloxy group, ethyl sulfonyloxy group, t-butyl sulfonyloxy group or the like;

a haloalkyl sulfonyloxy group such as trifluoromethyl sulfonyloxy group, 2,2,2-trifluoroethyl sulfonyloxy group or the like;

a tri C1-6 alkyl substituted silyl group such as trimethyl silyl group, triethyl silyl group, t-butyl dimethyl silyl group or the like;

a tri C6-10 aryl substituted silyl group such as triphenyl silyl group or the like; a cyano group; a nitro group.

In addition, any of the hydrogen atoms in these "substituents" may be substituted with other substituents having a different structure. In this case, examples of the "substituents" include a C1-6 alkyl group, C1-6 haloalkyl group, C1-6 alkoxy group, C1-6 haloalkoxy group, halogeno group, cyano group, nitro group and the like.

In addition, the above described "3-6 membered heterocyclyl group" is a group having 1-4 hetetro atoms selected from the group consisting of a nitrogen atom, oxygen atom and sulfur atom as a constitution atom of the ring. The heterocyclyl group may be a monoheterocyclyl group or a polyheterocyclyl group. As long as the polyheterocyclyl group includes at least one hetero ring, the remaining ring may be a saturated alicyclic ring, an unsaturated alicyclic ring or an aromatic ring. Examples of the "3-6 membered heterocyclyl group" include a 3-6 membered saturated heterocyclyl group, 5-6 membered heteroaryl group, 5-6 membered partially-unsaturated heterocyclyl group and the like.

Examples of the "3-6 membered saturated heterocyclyl group" include an aziridinyl group, epoxy group, pyrrolidinyl group, tetrahydrofuranyl group, thiazolidinyl group, piperidyl group, piperazinyl group, morpholinyl group, dioxolanyl group, dioxanyl group and the like.

Examples of the "5 membered heteroaryl group" include a pyrrolyl group, furyl group, thienyl group, imidazolyl group, pyrazolyl group, oxazolyl group, isoxazolyl group, thiazolyl group, isothiazolyl group, triazolyl group, oxadiazolyl group, thiadiazolyl group, tetrazolyl group and the like.

Examples of the "6 membered heteroaryl group" include a pyridyl group, pyrazinyl group, pyrimidinyl group, pyridazinyl group, triazinyl group and the like.

[$A^1$, $A^2$]

$A^1$ and $A^2$ each independently represents a nitrogen atom or $CR^3$, provided that $A^1$ and $A^2$ do not simultaneously represent a nitrogen atom or simultaneously represent $CR^3$.

That is, the compound represented by formula (I) may be the compounds represented by the following formulas (II) to (V).

[Chemical formula 6]

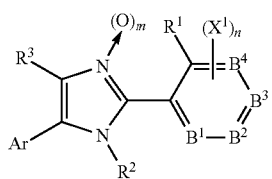

(II)

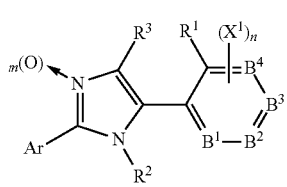

(III)

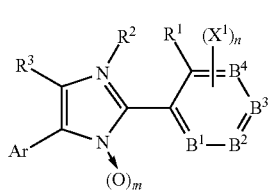

(IV)

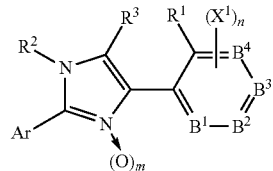

(V)

In formulas (II) to (III), $B^1$, $B^2$, $B^3$, $B^4$, $X^1$, $R^1$, $R^2$, $R^3$, n, m and Ar are as defined in formula (I).

[$B^1$, $B^2$, $B^3$, $B^4$]

$B^1$, $B^2$, $B^3$ and $B^4$ each independently represents a carbon atom or a nitrogen atom, provided that when $B^1$ is a nitrogen atom, $B^2$ and $B^4$ represent a carbon atom and $B^3$ represents a carbon atom or a nitrogen atom, and when $B^1$ is a carbon atom, $B^2$ to $B^4$ represent a carbon atom or a nitrogen atom except that two or more of $B^2$ to $B^4$ simultaneously represent a nitrogen atom.

That is, the compound represented by formula (I) may be the compounds represented by the following formulas (a) to (f).

[Chemical formula 7]

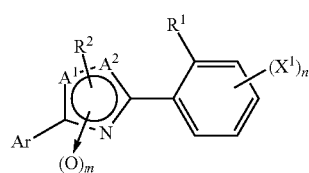

(a)

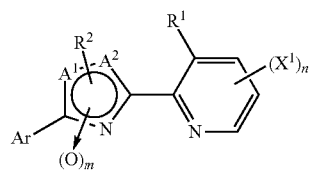

(b)

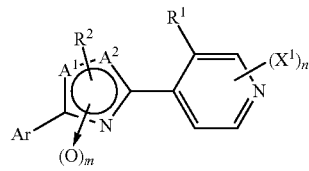

(c)

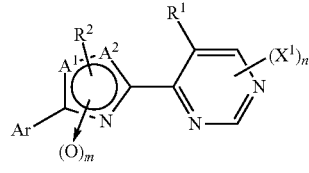

(d)

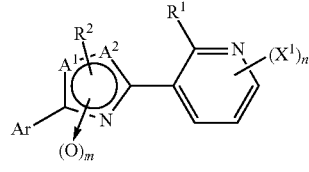

(e)

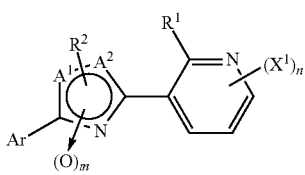

(f)

In formulas (a) to (f), $A^1$, $A^2$, $X^1$, $R^1$, $R^2$, $R^3$, n, m and Ar are as defined in formula (I).

Among these compounds, the compound represented by formula (I), wherein $B^1$ represents a nitrogen atom or a carbon atom, $B^2$, $B^3$ and $B^4$ represent a carbon atom, namely the compounds represented by formulas (a) and (b) are preferable.

[$X^1$, n]

$X^1$ represents an unsubstituted or substituted C1-6 alkyl group, unsubstituted or substituted C2-6 alkenyl group, unsubstituted or substituted C2-6 alkynyl group, hydroxy group, unsubstituted or substituted C1-6 alkoxy group, formyl group, unsubstituted or substituted C1-6 alkyl carbonyl group, unsubstituted or substituted C1-6 alkoxycarbonyl group, unsubstituted or substituted C1-6 alkyl aminocarbonyl group, mercapto group, unsubstituted or substituted C1-6 alkyl thio group, unsubstituted or substituted C1-6 alkyl sulfinyl group, unsubstituted or substituted C1-6 alkyl sulfonyl group, unsubstituted or substituted C3-8 cycloalkyl group, unsubstituted or substituted C6-10 aryl group, unsubstituted or substituted 3-6 membered heterocyclyl group, unsubstituted or substituted amino group, halogen group, cyano group or nitro group.

The "C1-6 alkyl group" of $X^1$ may be a linear alkyl group or a branched alkyl group when the carbon number is three or more. Examples of the "alkyl group" include a methyl group, ethyl group, n-propyl group, n-butyl group, n-pentyl group, n-hexyl group, i-propyl group, i-butyl group, s-butyl group, t-butyl group, i-pentyl group, neopentyl group, 2-methyl butyl group, 2, 2-dimethyl propyl group, i-hexyl group and the like.

Specific examples of the "substituted C1-6 alkyl group" include a C1-6 haloalkyl group such as fluoromethyl group, chloromethyl group, bromomethyl group, difluoromethyl group, dichloromethyl group, dibromomethyl group, trifluoromethyl group, trichloromethyl group, tribromomethyl group, 1-chloroethyl group, 2,2,2-trifluoroethyl group, 2,2,2-trichloroethyl group, pentafluoroethyl group, 4-fluorobutyl group, 4-chlorobutyl group, 3,3,3-trifluoropropyl group, 2,2,2-trifluoro-1-trifluoromethyl ethyl group, 1,1,1,3,3,3-hexafluoropropane-2-yl group, perfluoropropane-2-yl group, perfluorohexyl group, perchlorohexyl group, 2,4,6-trichlorohexyl group or the like;

a hydroxy C1-6 alkyl group such as hydroxymethyl group, hydroxyethyl group or the like;

a C1-6 alkoxy C1-6 alkyl group such as methoxymethyl group, ethoxymethyl group, methoxyethyl group, ethoxyethyl group, methoxy-n-propyl group, n-propoxymethyl group, i-propoxyethyl group, s-butoxymethyl group, t-butoxyethyl group or the like;

a C6-10 aryl C1-6 alkyl group such as benzyl group, phenethyl group or the like;

a C3-8 cycloalkyl C1-6 alkyl group such as cyclopropyl methyl group, 2-cyclopropyl ethyl group, cyclopentyl methyl group, 2-cyclohexyl ethyl group, 2-cyclooctyl ethyl group or the like; and the like.

Examples of the "C2-6 alkenyl group" of $X^1$ include a vinyl group, 1-propenyl group, 2-propenyl group, 1-butenyl group, 2-butenyl group, 3-butenyl group, 1-methyl-2-propenyl group, 2-methyl-2-propenyl group, 1-pentenyl group, 2-pentenyl group, 3-pentenyl group, 4-pentenyl group, 1-methyl-2-butenyl group, 2-methyl-2-butenyl group, 1-hexenyl group, 2-hexenyl group, 3-hexenyl group, 4-hexenyl group, 5-hexenyl group and the like.

Specific examples of the "substituted C2-6 alkenyl group" include a C2-6 haloalkenyl group such as a 2-chloro-1-propenyl group, 2-fluoro-1-butenyl group or the like; a C1-6 alkoxy C2-6 alkenyl group such as a 2-n-butoxy-vinyl group, 1-ethoxy-vinyl group or the like; and the like.

Examples of the "C2-6 alkynyl group" of $X^1$ include an ethynyl group, 1-propynyl group, 2-propynyl group, 1-butynyl group, 2-butynyl group, 3-butynyl group, 1-methyl-2-propynyl group, 2-methyl-3-butynyl group, 1-pentynyl group, 2-pentynyl group, 3-pentynyl group, 4-pentynyl group, 1-methyl-2-butynyl group, 2-methyl-3-pentynyl group, 1-hexynyl group, 1,1-dimethyl-2-butynyl group and the like.

Specific examples of the "substituted C2-6 alkynyl group" include a C2-6 haloalkynyl group such as 4,4-dichloro-1-butynyl group, 4-fluoro-1-pentynyl group, 5-bromo-2-pentynyl group or the like; and the like.

Examples of the "C1-6 alkoxy group" of $X^1$ include a methoxy group, ethoxy group, n-propoxy group, n-butoxy group, n-pentyloxy group, n-hexyloxy group, i-propoxy group, i-butoxy group, s-butoxy group, t-butoxy group, i-hexyloxy group and the like.

Specific examples of the "substituted C1-6 alkoxy group" include a C1-6 haloalkoxy group such as a trifluoromethoxy group, difluoromethoxy group, 1-fluoroethoxy group, 1,1-difluoroethoxy group, 2,2,2-trifluoroethoxy group, pentafluoroethoxy group, 2,2,3,4,4,4-hexafluoro-butoxy group, chloromethoxy group, dichloromethoxy group, trichloromethoxy group or the like;

a C1-6 alkoxy C1-6 alkoxy group such as a methoxymethoxy group, methoxyethoxy group or the like;

a C6-10 aryl C1-6 alkoxy group such as a benzyloxy group, phenethyloxy group or the like; and a C3-8 cycloalkyl C1-6 alkoxy group such as a cyclopropyl methyloxy group or the like.

Examples of the "C1-6 alkylcarbonyl group" of $X^1$ include an acetyl group, propionyl group and the like.

Specific examples of the "substituted C1-6 alkylcarbonyl group" include a C1-6 haloalkyl carbonyl group such as a chloroacetyl group, trifluoroacetyl group, trichloroacetyl group or the like.

Examples of the "C1-6 alkoxycarbonyl group" of $X^1$ include a methoxycarbonyl group, ethoxycarbonyl group, n-propoxycarbonyl group, i-propoxycarbonyl group, t-butoxycarbonyl group and the like.

Specific examples of the "substituted C1-6 alkoxycarbonyl group" include a C1-6 haloalkoxycarbonyl group such as a fluoromethoxycarbonyl group, chloromethoxycarbonyl group, bromomethoxycarbonyl group, difluoromethoxycarbonyl group, dichloromethoxycarbonyl group, dibromomethoxycarbonyl group, trifluoromethoxycarbonyl group, trichloromethoxycarbonyl group, tribromomethoxycarbonyl group, 2,2,2-trifluoroethoxycarbonyl group or the like;

a C3-8 cycloalkyl C1-6 alkoxycarbonyl group such as a cyclopropyl methoxycarbonyl group, cyclobutyl methoxycarbonyl group, cyclopentyl methoxycarbonyl group, cyclohexyl methoxycarbonyl group, 2-cyclopropyl ethoxycarbonyl group or the like; and the like.

Examples of the "C1-6 alkyl aminocarbonyl group" of $X^1$ include a methyl aminocarbonyl group, ethyl aminocarbonyl group, butyl aminocarbonyl group, dimethyl aminocarbonyl group, diethyl aminocarbonyl group, N-butyl-N-methyl aminocarbonyl group and the like.

Examples of the "C1-6 alkyl thio group" of $X^1$ include a methyl thio group, ethyl thio group, n-propyl thio group, n-butyl thio group, n-pentyl thio group, n-hexyl thio group, i-propyl thio group, i-butyl thio group and the like.

Specific examples of the "substituted C1-6 alkyl thio group" include a C1-6 haloalkyl thio group such as a trifluoromethyl thio group, 2,2,2-trifluoroethyl thio group or the like.

Examples of the "C1-6 alkyl sulfinyl group" of $X^1$ include a methyl sulfinyl group, ethyl sulfinyl group, t-butyl sulfinyl group and the like.

Specific examples of the "substituted C1-6 alkyl sufinyl group" include a C1-6 haloalkyl sulfinyl group such as a trifluoromethyl sulfinyl group, 2,2,2-trifluoroethyl sulfinyl group or the like.

Examples of the "C1-6 alkyl sulfonyl group" of $X^1$ include a methyl sulfonyl group, ethyl sulfonyl group, t-butyl sulfonyl group and the like.

Specific examples of the "substituted C1-6 alkyl sulfonyl group" include a C1-6 haloalkyl sulfonyl group such as a trifluoromethyl sulfonyl group, 2,2,2-trifluoroethyl sulfonyl group or the like.

Examples of the substituents on the "C1-6 alkyl group", "C2-6 alkenyl group", "C2-6 alkynyl group", "C1-6 alkoxy group", "C1-6 alkyl carbonyl group", "C1-6 alkoxycarbonyl group", "C1-6 alkyl thio group", "C1-6 alkyl sulfinyl group", "C1-6 alkyl sulfonyl group" of $X^1$ include a C1-6 alkoxy group, halogeno group, cyano group, hydroxy group, C3-8 cycloalkyl group, C6-10 aryl group, 3-6 membered heterocyclyl group and the like.

Examples of the "C3-8 cycloalkyl group" of $X^1$ include a cyclopropyl group, cyclobutyl group, cyclopentyl group, cyclohexyl group, cycloheptyl group and the like.

The "C6-10 aryl group" of $X^1$ may be a monocyclic ring or polycyclic ring. If the polycyclic aryl group has at least one aromatic ring, the remaining rings may be a saturated alicyclic ring, an unsaturated alicyclic ring or an aromatic ring.

Examples of the "C6-10 aryl group" include a phenyl group, naphthyl group, azulenyl group, indenyl group, indenyl group, tetralinyl group and the like.

The "3-6 membered heterocyclyl group" of $X^1$ is a group having 1-4 hetetro atoms selected from the group consisting of a nitrogen atom, oxygen atom and sulfur atom as a constitution atom of the ring. The heterocyclyl group may be a monoheterocyclyl group or a polyheterocyclyl group. As long as the polyheterocyclyl group includes at least one hetero ring, the remaining ring may be a saturated alicyclic ring, an unsaturated alicyclic ring or an aromatic ring. Examples of the "3-6 membered heterocyclyl group" include a 3-6 membered saturated heterocyclyl group, 5-6 membered heteroaryl group, 5-6 membered partially-unsaturated heterocyclyl group and the like.

Examples of the "3-6 membered saturated heterocyclyl group" include an aziridinyl group, epoxy group, pyrrolidinyl group, tetrahydrofuranyl group, thiazolidinyl group, piperidyl group, piperazinyl group, morpholinyl group, dioxolanyl group (specifically, [1,3]dioxolanyl group), dioxanyl group (specifically, [1,3]dioxanyl group or [1,4] dioxanyl group) and the like. Among these examples, 5-6 membered saturated heterocyclyl group is preferable.

Examples of the "5 membered heteroaryl group" include a pyrrolyl group, furyl group, thienyl group, imidazolyl group, pyrazolyl group, oxazolyl group, isoxazolyl group, thiazolyl group, isothiazolyl group, triazolyl group (specifically, [1,2,3]triazolyl group or [1,2,4]triazolyl group), oxadiazolyl group (specifically, [1,2,4]oxadiazolyl group or [1,3,4]oxadiazolyl group), thiadiazolyl group, tetrazolyl group and the like.

Examples of the "6 membered heteroaryl group" include a pyridyl group, pyrazinyl group, pyrimidinyl group, pyridazinyl group, triazinyl group and the like.

The "partially unsaturated 5 membered heterocyclyl group" include a pyrrolinyl group, imidazolinyl group (dihydroimidazolyl group), pyrazolinyl group, oxazolinyl group, isoxazolinyl group, thiazolinyl group and the like.

The "partially unsaturated 6 membered heterocyclyl group" include a thiopyranyl group, 2H-pyridine-1-yl group, 4H-pyridine-1-yl group and the like.

The substituents on the "C3-8 cycloalkyl group", "C6-10 aryl group" and "3 to 6 membered heterocyclyl group" of $X^1$ include a C1-6 alkyl group, C1-6 haloalkyl group, hydroxy group, C1-6 alkoxy group, halogeno group, cyano group, nitro group and the like.

Examples of the "substituted amino group" of $X^1$ include a C1-6 alkyl substituted amino group such as a methyl amino group, n-butyl amino group, dimethyl amino group, diethyl amino group or the like.

Examples of the "halogeno group" of $X^1$ include a fluoro group, chloro group, bromo group, iodo group and the like.

As $X^1$, a C1-6 alkyl group, C1-6 haloalkyl group, C1-6 haloalkoxy group, hydroxy C1-6 alkyl group, C1-6 alkoxycarbonyl group, C1-6 alkyl sulfonyl group, halogeno group, cyano group and formyl group are preferable, and a C1-6 haloalkyl group is more preferable.

n represents a chemically acceptable number of $X^1$ and represents an integer of 0 to 4. When n is 2 or more, $X^1$'s may be the same or different. When $B^1$, $B^2$, $B^3$ and $B^4$ represent a carbon atom, namely the compound is represented by formula (a), n is an integer of 0 to 4. When at least one of $B^1$, $B^2$, $B^3$ and $B^4$ represents a nitrogen atom, namely the compound is represented by formula (b), (c), (e) or (f), n is an integer of 0 to 3. When $B^1$ and $B^3$ represent a nitrogen atom and $B^2$ and $B^4$ represent a carbon atom, namely the compound is represented by formula (b), n is integer of 0 to 2.

n is preferably an integer of 0 to 2, more preferably 0 or 1.

When n is 2 or more, two $X^1$s may bond together to form a ring.

[$R^1$]

$R^1$ represents a halogeno group, hydroxy group, cyano group, substituted C1-6 alkyl group, unsubstituted or substituted C1-6 alkoxy group, unsubstituted or substituted C1-6 alkyl thio group, unsubstituted or substituted C1-6 alkyl sulfinyl group, unsubstituted or substituted C1-6 alkyl sulfonyl group, unsubstituted or substituted C1-6 alkyl sulfonyloxy group, C1-6 alkyl aminocarbonyl group, C1-6 alkylsulfoximino group or a group represented by —S(=O)(=N—$R^a$)—$R^b$.

In the formula, $R^a$ represents a hydrogen atom, cyano group, C1-6 alkyl group, or unsubstituted or substituted C1-6 alkyl carbonyl group, $R^b$ represents a C1-6 alkyl.

The "halogeno group", "C1-6 alkyl aminocarbonyl group", "C1-6 alkyl thio group", "C1-6 alkyl sulfinyl group", "C1-6 alkyl sulfonyl group" and the groups having substituents thereon of $R^1$ may be the same as the examples of $X^1$ listed above.

Examples of the "substituted C1-6 alkyl group" of $R^1$ may be the same as the examples of $X^1$ listed above, and may also be a C1-6 alkyl substituted aminocarbonyl C1-6 alkyl group such as a methyl aminocarbonyl methyl group, dimethyl aminocarbonyl methyl group or the like.

Examples of the "unsubstituted or substituted C1-6 alkoxy group" of $R^1$ may be the same as the examples of $X^1$ listed above, and may also be a C1-6 alkoxy C1-6 alkoxy group such as a methoxymethoxy group, methoxyethoxy group, ethoxymethoxy group or the like;

a C1-6 alkyl thio C1-6 alkoxy group such as a methyl thiomethoxy group, ethyl thiomethoxy group or the like;

a C1-6 alkyl sulfinyl C1-6 alkoxy group such as a methyl sulfinyl methoxy group, ethyl sulfinyl methoxy group or the like;

a C1-6 alkyl sulfonyl C1-6 methoxy group such as a methyl sulfonyl methoxy group, ethyl sulfonyl methoxy group or the like.

Examples of the "C1-6 alkyl sulfonyloxy group" of $R^1$ include a methyl sulfonyloxy group, ethyl sulfonyloxy group, t-butyl sulfonyloxy group and the like.

Specific examples the "substituted C1-6 alkyl sulfonyloxy group" include a C1-6 haloalkyl sulfonyloxy group such as a trifluoromethyl sulfonyloxy group, 2,2,2-trifluoroethyl sulfonyloxy group or the like.

Examples of the "C1-6 alkyl sulfoxyimino group" include a S,S-dimethyl sulfoxyimino group and the like.

Examples of the "C1-6 alkyl group", "C1-6 alkyl carbonyl group" of $R^a$ and $R^b$ in formula —S(=O)(=N—$R^a$)—$R^b$ are the same as the examples of $X^1$ listed above. As the "substituted C1-6 alkyl carbonyl group" of $R^a$, C1-6 haloalkyl carbonyl group is preferable.

As $R^1$, a halogeno group, hydroxy group, cyano group, C1-6 alkoxy group, C1-6 haloalkoxy group, C1-6 alkoxy C1-6 alkoxy group, C1-6 alkyl thio C1-6 alkoxy group, C1-6 alkyl sulfinyl C1-6 alkoxy group, C1-6 alkyl sulfonyl C1-6 alkoxy group, C1-6 alkyl thio group, C1-6 haloalkyl thio group, C1-6 alkyl sulfinyl group, C1-6 haloalkyl sulfinyl group, C1-6 alkyl sulfonyl group, C1-6 haloalkyl sulfonyl group, C1-6 alkyl sulfonyloxy group, C1-6 alkyl aminocarbonyl group, C1-6 alkyl sufoxyimino group and a group represented by formula —S(=O)(=N—$R^a$)—$R^b$ are preferable, and a C1-6 alkyl thio group, C1-6 alkyl sulfinyl group and C1-6 alkyl sulfonyl group are more preferable.

[$R^2$, m]

$R^2$ represents an unsubstituted or substituted C1-6 alkyl group, unsubstituted or substituted C2-6 alkenyl group, unsubstituted or substituted C2-6 alkynyl group, unsubstituted or substituted C3-8 cycloalkyl group, hydroxy group, unsubstituted or substituted C1-6 alkoxy group, formyl group, unsubstituted or substituted C1-6 alkyl carbonyl group, unsubstituted or substituted C1-6 alkoxycarbonyl group, or unsubstituted or substituted C1-6 alkyl sulfonyl group. $R^2$ is a substituent bonding with any one of the two nitrogen atoms on the imidazole ring, Examples of the "C1-6 alkyl group", "C2-6 alkenyl group", "C2-6 alkynyl group", "C3-8 cycloalkyl group", "C1-6 alkoxy group", "C1-6 alkyl carbonyl group", "C1-6 alkoxycarbonyl group", "C1-6 alkyl sulfonyl group" and the groups having substituent thereon of $R^2$ are the same as the examples of $X^1$ listed above.

As $R^2$, a C1-6 alkyl group, C3-8 cycloalkyl group (preferably a C3-6 cycloalkyl group), C1-6 haloalkyl group, C1-6 alkoxy group and hydroxy group are preferable, and a C1-6 alkyl group is more preferable.

m represents a number of the oxide group bonding with the nitrogen atom which does not bond with $R^2$ on the imidazole ring, and represents 0 or 1. m is preferably 0.

[$R^3$]

$R^3$ represents a hydrogen atom, unsubstituted or substituted C1-6 alkyl group, unsubstituted or substituted C6-10 aryl group, halogen group, cyano group or nitro group.

Examples of the "C1-6 alkyl group", "C6-10 aryl group", "halogen group" and the groups having substituents thereon of $R^3$ are the same as the examples of $X^1$ listed above.

As $R^3$, a hydrogen atom, halogeno group and C1-6 alkyl group are preferable, and a hydrogen atom is more preferable.

[Ar]

Ar represents an unsubstituted or substituted C6-10 aryl group or unsubstituted or substituted 5-10 membered heteroaryl group.

Examples of the "C6-10 aryl group" of Ar are the same as the examples of $X^1$ listed above.

Examples of the "5-10 membered heteroaryl group" may be the same as the examples of 5 membered heteroaryl group and 6 membered heteroaryl group listed as the examples of $X^1$, and may also be a 9 membered heteroaryl group such as an indolyl group, isoindolyl group, benzofuranyl group, indazolyl group, benzoxazolyl group, benzisoxazolyl group, benzothiazolyl group, benzisothiazolyl group or the like; a 10 membered heteroaryl group such as a quinolinyl group, isoquinolinyl group, cinnolinyl group, phthalazinyl group, quinazolinyl group, quinoxalinyl group or the like; or the like.

As Ar, a phenyl group, thienyl group, pyrazolyl group, thiazolyl group, pyridyl group, pyrimidyl group, pyridazinyl group and quinolinyl group are preferable, and a phenyl group is more preferable.

Examples of the substituents on the "C6-10 aryl group" and "5-10 membered heteroaryl group" of Ar include a C1-6 alkyl group, C1-6 haloalkyl group, hydroxy group, C1-6 alkoxy group, C1-6 haloalkoxy group, C1-6 alkoxy C1-6 haloalkyl group, C1-6 alkoxy C1-6 alkoxy group, C1-6 alkyl thio group, C1-6 haloalkyl thio group, C1-6 haloalkyl sulfinyl group, C1-6 haloalkyl sulfonyl group, C1-6 haloalkyl sulfonyloxy group, unsubstituted or substituted 5-6 membered heteroaryl group, unsubstituted or substituted C6-10 aryl group, C1-6 haloalkylene dioxy group, halogeno group, cyano group, nitro group, amino group, pentafluorosulfanyl group and the like.

Examples of the "C1-6 alkyl group, C1-6 haloalkyl group, C1-6 alkoxy group, C1-6 haloalkoxy group, C1-6 alkyl thio group, C1-6 haloalkyl thio group, C1-6 haloalkyl sulfinyl group, C1-6 haloalkyl sulfonyl group, C1-6 haloalkyl sulfonyloxy group, 5-6 membered heteroaryl group and C6-10 aryl group" as the substituents on the "C6-10 aryl group" and "5-10 membered heteroaryl group" of Ar are the same as the examples of $X^1$ listed above.

Examples of the "C1-6 alkoxy C1-6 haloalkyl group" include a methoxydifluoromethyl group, 2,2,2-trifluoro-1-methoxy-1-trifluoromethyl ethyl group, 1,1,1,3,3,3-hexafluoro-2-methoxy-propane-2-yl group and the like.

Examples of the "C1-6 haloalkylene dioxy group" include a difluoromethylene dioxy group (—$OCF_2O$—), tetrafluoroethylene dioxy group (—$OCF_2CF_2O$—) and the like. Examples of the "C1-6 haloalkylene dioxy group substituted C6-10 aryl group" include a 2,2,3,3-tetrafluoro-2,3-dihydro-benzo [1,4]dioxyl group, 2,2-difluoro-benzo [1,3]dioxolyl group and the like.

As the substituents on the "C6-10 aryl group" and "5-10 membered heteroaryl group" of Ar, a C1-6 alkyl group, C1-6 haloalkyl group, C1-6 alkoxy group, C1-6 haloalkoxy group, C1-6 alkoxy C1-6 haloalkyl group, C1-6 alkoxy C1-6 alkoxy group, C1-6 alkyl thio group, C1-6 haloalkyl thio group, C1-6 haloalkyl sulfinyl group, C1-6 haloalkyl sulfonyl group, C1-6 haloalkyl sulfonyloxy group, unsubstituted or substituted 5-6 membered heteroaryl group (preferably a C1-6 haloalkyl group), unsubstituted or substituted C6-10 aryl group (preferably a C1-6 haloalkyl group), C1-6 haloalkylene dioxy group, halogeno group, cyano group, nitro group, amino group and pentafluorosulfanyl group are preferable, and a C1-6 haloalkyl group, C1-6 haloalkoxy group, C1-6 alkyl thio group, C1-6 haloalkyl thio group, C1-6 haloalkyl sulfonyl group, C1-6 haloalkylene dioxy group, halogen group, nitro group and cyano group are more preferable.

As the number of the substituents on the "C6-10 aryl group" and "5-10 membered heteroaryl group" of Ar, 0 to 3 are preferable, and 1 or 2 is more preferable.

As compound (I), a compound represented by formula (I), wherein $R^2$ and $R^3$ are not adjacent, namely a compound represented by formula (II) or formula (III) is preferable.

[Chemical formula 8]

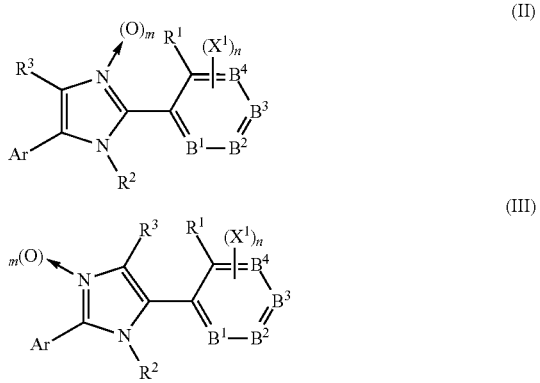

[in formula (II), $X^1$, $R^1$, $R^2$, $R^3$, $B^1$, $B^2$, $B^3$, $B^4$, n, m and Ar are as defined in formula (I).]

There are no particular limitations on the salt of compound (I) provided that it is an agriculturally and horticulturally acceptable salt. Examples of the salt include salts of inorganic acids such as a hydrochloric acid, sulfuric acid or the like; salts of organic acids such as an acetic acid, lactic acid or the like; salts of alkaline metals such as a lithium, sodium, potassium or the like; salts of alkaline earth metals such as a calcium, magnesium or the like; salts of transition metals such as an iron, copper or the like; salts of organic bases such as an ammonia, triethylamine, tributylamine, pyridine, hydrazine or the like; and the like.

The compound (I) or salt thereof is not particularly limited by the production method thereof. In addition, the salt of compound (I) may be produced from compound (I) by a well-known method. For example, compound (I) or salt thereof may be obtained by the well-known production method described in the working examples The diarylimidazole compound of the present invention has a superior effect for preventing harmful organisms such as various agricultural pests affecting the plant growth, acari or the like.

In addition, the diarylimidazole compound of the present invention has a high safety because it does not have phytotoxicity against plants and has a low level of toxicity against fishes or warm-blooded animals. Therefore, the diarylimidazole compound of the present invention is useful for an active ingredient of pesticide or acaricide.

More over, in recent years, many pests such as diamondback moths, planthoppers, leafhoppers and aphids have developed a resistance to the organic phosphorous agents and carbamate agents, and because of this, the efficacy of the traditional agrochemicals has become insufficient, new agrochemicals that are effective even for preventing the resistant strains of pests are desired. The diarylimidazole compound of the present invention demonstrates superior efficacy for preventing the sensitive strains of pests, and also for preventing the various resistant strains of pests and acaricide-resistant strains of acari.

The diarylimidazole compound of the present invention has a superior effect for preventing the external and internal parasites harmful for humans and animals. More over, the diarylimidazole compound of the preset invention is a highly safe compound, because it has a low level of toxicity to the fishes or warm-blooded animals. Therefore, the diarylimidazole compound of the present invention is useful as an active ingredient of external and internal parsite control agent.

In addition, the diarylimidazole compound of the present invention is effective for preventing the targeted organisms in any development stages, for example, acari and insect in the stages of eggs, nymph, larvae, pupa and adult.

[Harmful Organism Control Agent, Insecticide or Acaricide]

The harmful organism control agent, insecticide or acaricide of the present invention include at least one compound of the diarylimidazole compound of the present invention as an active ingredient. The amount of the diarylimidazole compound included in the harmful organism control agent, insecticide or acaricide of the present invention is not particularly limited as long as it demonstrates prevention effects against the harmful organisms.

The harmful organism control agent, insecticide or acaricide of the present invention are preferably used for crops; green stuff; edible roots; tuber crops; froot trees; trees of tea, coffee, cacao or the like; grasses for pastures; grasses for lawns; plants such as cotton; or the like.

As for the application to the plants, the harmful organism control agent, insecticide or acaricide of the present invention may be applied on any one part of the plants, such as leaf, stem, stalk, flower, bud, fruit, seed, sprout, root, tuber, tuberous root, shoot, cutting and the like. In addition, although the plant varieties for which the harmful organism control agent, insecticide or acaricide of the present invention is applicable are not particularly limited, examples of the plant varieties include the originals, varieties, improved varieties, cultivated varieties, mutant plants, hydrid plants, genetically-modified plants (GMO) and the like.

The harmful organism control agent of the present invention can be used for preventing various agricultural pests and acari by seed treatment, foliar spraying, soil application or water surface application and the like.

Specific examples of the various agricultural pests and acari which can be prevented by the harmful organism control agent of the present invention include the followings.

(1) Butterfly or Moth of Lepidoptera Order (a) moth belonging to the Arctiidae family, for example, *Hyphantria cunea, Lemyra imparilis;*

(b) moth belonging to the Bucculatricidae family, for example, *Bucculatrix pyrivorella;*

(c) moth belonging to the Carposinidae family, for example, *Carposina sasakii;*

(d) moth belonging to the Crambidae family, for example, *Diaphania indica* and *Diaphania nitidalis* of *Diaphania* spp.; for example, *Ostrinia furnacalis*, *Ostrinia nubilalis* and *Ostrinia scapulalis* of *Ostrinia* spp.; Others such as *Chilo suppressalis, Cnaphalocrocis medinalis, Conogethes punctiferalis, Diatraea grandiosella, Glyphodes pyloalis, Hellula undalis, Parapediasia teterrella*;

(e) moth belonging to the Gelechiidae family, for example, *Helcystogramma triannulella, Pectinophora gossypiella, Phthorimaea operculella, Sitotroga cerealella*;

(f) moth belonging to the Geometridae family, for example, *Ascotis selenaria*;

(g) moth belonging to the Gracillariidae family, for example, *Caloptilia theivora, Phyllocnistis citrella, Phyllonorycter ringoniella*;

(h) butterfly belonging to the Hesperiidae family, for example, *Pamara guttata*;

(i) moth belonging to the Lasiocampidae family, for example, *Malacosoma neustria*;

(j) moth belonging to the Lymantriidae family, for example, *Lymantria dispar* and *Lymantria monacha* of *Lymantria* spp.; Others such as *Euproctis pseudoconspersa, Orgyia thyellina*;

(k) moth belonging to the Lyonetiidae family, for example, *Lyonetia clerkella* and *Lyonetia prunifoliella malinella* of *Lyonetia* spp.;

(l) moth belonging to the Noctuidae family, for example, *Spodoptera depravata, Spodoptera eridania, Spodoptera exigua, Spodoptera frugiperda, Spodoptera littoralis* and *Spodoptera litura* of *Spodoptera* spp.; for example, *Autographa gamma* and *Autographa nigrisigna* of *Autographa* spp.; for example, *Agrotis ipsilon* and *Agrotis segetum* of *Agrotis* spp.; for example, *Helicoverpa armigera, Helicoverpa assulta* and *Helicoverpa zea* of *Helicoverpa* spp.; for example, *Heliothis armigera* and *Heliothis virescens* of *Heliothis* spp.; Others such as *Aedia leucomelas, Ctenoplusia agnata, Eudocima tyrannus, Mamestra brassicae, Mythimna separata, Naranga aenescens, Panolis japonica, Peridroma saucia, Pseudoplusia includens, Trichoplusia ni*;

(m) moth belonging to the Nolidae family, for example, *Earias insulana*;

(n) butterfly belonging to the Pieridae family, for example, *Pieris brassicae* and *Pieris rapae crucivora* of *Pieris* spp.;

(o) moth belonging to the Plutellidae family, for example, *Acrolepiopsis sapporensis* and *Acrolepiopsis suzukiella* of *Acrolepiopsis* spp.; others such as *Plutella xylostella*;

(p) moth belonging to the Pyralidae family, for example, *Cadra cautella, Elasmopalpus lignosellus, Etiella zinckenella, Galleria mellonella*;

(q) moth belonging to the Sphingidae, for example, *Manduca quinquemaculata* and *Manduca sexta* of *Manduca* spp.;

(r) moth belonging to the Stathmopodidae family, for example, *Stathmopoda masinissa*;

(s) moth belonging to the Tineidae family, for example, *Tinea translucens*;

(t) moth belonging to the Tortricidae family, for example, *Adoxophyes honmai* and *Adoxophyes orana* of *Adoxophyes* spp.; for example, *Archips breviplicanus* and *Archips fuscocupreanus Archips* spp.; others such as *Choristoneura fumiferana, Cydia pomonella, Eupoecilia ambiguella, Grapholitha molesta, Homona magnanima, Leguminivora glycinivorella, Lobesia botrana, Matsumuraeses phaseoli, Pandemis heparana, Sparganothis pilleriana*;

(u) moth belonging to the Yponomeutidae family, for example, *Argyresthia conjugella*.

(2) Pest of Thysanoptera Order (a) pest belonging to the Phlaeothripidae family, for example, *Ponticulothrips diospyrosi*;

(b) pest belonging to the Thripidae family, for example, *Frankliniella intonsa* and *Frankliniella occidentalis* of *Frankliniella* spp.; for example, *Thrips palmi* and *Thrips tabaci* of *Thrips* spp.; others such as *Heliothrips haemorrhoidalis, Scirtothrips dorsalis*.

(3) Pest of Hemiptera Order (A) Archaeorrhyncha Suborder (a) pest belonging to the Delphacidae family, for example, *Laodelphax striatella, Nilaparvata lugens, Perkinsiella saccharicida, Sogatella furcifera*.

(B) Clypeorrhyncha Suborder (a) pest belonging to the Cicadellidae family, for example, *Empoasca fabae, Empoasca nipponica, Empoasca onukii* and *Empoasca sakaii* of *Empoasca* spp.; others such as *Arboridia apicalis, Balclutha saltuella, Epiacanthus stramineus, Macrosteles striifrons, Nephotettix cinctinceps*.

(C) Heteroptera Suborder (a) pest belonging to the Alydidae family, for example, *Riptortus clavatus*;

(b) pest belonging to the Coreidae family, for example, *Cletus punctiger, Leptocorisa chinensis*;

(c) pest belonging to the Lygaeidae family, for example, *Blissus leucopterus, Cavelerius saccharivorus, Togo hemipterus*;

(d) pest belonging to the Miridae family, for example, *Halticus insularis, Lygus lineolaris, Psuedatomoscelis seriatus, Stenodema sibiricum, Stenotus rubrovittatus, Trigonotylus caelestialium*;

(e) pest belonging to the Pentatomidae family, for example, *Nezara antennata* and *Nezara viridula* of *Nezara* spp.; for example, *Eysarcoris aeneus, Eysarcoris lewisi* and *Eysarcoris ventralis* of *Eysarcoris* spp.; others such as *Dolycoris baccarum, Eurydema rugosum, Glaucias subpunctatus, Halyomorpha halys, Piezodorus hybneri, Plautia crossota, Scotinophora lurida*;

(f) pest belonging to the Pyrrhocoridae family, for example, *Dysdercus cingulatus*;

(g) pest belonging to the Rhopalidae family, for example, *Rhopalus msculatus*;

(h) pest belonging to the Scutelleridae family, for example, *Eurygaster integriceps*;

(i) pest belonging to the Tingidae family, for example, *Stephanitis nashi*.

(D) Sternorrhyncha Suborder (a) pest belonging to the Adelgidae family, for example, *Adelges laricis*;

(b) pest belonging to the Aleyrodidae family, for example, *Bemisia argentifolii, Bemisia tabaci* of *Bemisia* spp.; others such as *Aleurocanthus spiniferus, Dialeurodes citri, Trialeurodes vaporariorum*;

(c) pest belonging to the Aphididae family, for example, *Aphis craccivora, Aphis fabae, Aphis forbesi, Aphis gossypii, Aphis pomi, Aphis sambuci* and *Aphis spiraecola* of *Aphis* spp.; for example, *Rhopalosiphum maidis* and *Rhopalosiphum padi* of *Rhopalosiphum* spp.; for example, *Dysaphis plantaginea* and *Dysaphis radicola* of *Dysaphis* spp.; for example, *Macrosiphum avenae* and *Macrosiphum euphorbiae* of *Macrosiphum* spp.; for example, *Myzus cerasi, Myzus persicae* and *Myzus varians* of *Myzus* spp.; others such as *Acyrthosiphon pisum, Aulacorthum solani, Brachycaudus helichrysi, Brevicoryne brassicae, Chaetosiphon fragaefolii, Hyalopterus pruni, Hyperomyzus lactucae*,

*Lipaphis erysimi, Megoura viciae, Metopolophium dirhodum, Nasonovia ribis-nigri, Phorodon humuli, Schizaphis graminum, Sitobion avenae, Toxoptera aurantii;*

(d) pest belong to the Coccidae family, for example, *Ceroplastes ceriferus* and *Ceroplastes rubens* of *Ceroplastes* spp.;

(e) pest belonging to the Diaspididae family, for example, *Pseudaulacaspis pentagona* and *Pseudaulacaspis prunicola* of *Pseudaulacaspis* spp.; for example, *Unaspis euonymi* and *Unaspis yanonensis* of *Unaspis* spp.; others such as *Aonidiella aurantii, Comstockaspis perniciosa, Fiorinia theae, Pseudaonidia paeoniae;*

(f) pest belonging to the Margarodidae family, for example, *Drosicha corpulenta* and *Icerya purchasi;*

(g) pest belonging to the Phylloxeridae family, for example, *Viteus vitifolii;*

(h) pest belonging to the Pseudococcidae family, for example, *Planococcus citri* and *Planococcus kuraunhiae* of *Planococcus* spp.; others such as *Phenacoccus solani, Pseudococcus comstocki;*

(i) pest belonging to the Psyllidae family, for example, *Psylla mali* and *Psylla pyrisuga* of *Psylla* spp.; others such as *Diaphorina citri.*

(4) Pest of Polyphaga Suborder (a) pest belonging to the Anobiidae family, for example, *Lasioderma serricorne;*

(b) pest belonging to the Attelabidae family, for example, *Byctiscus betulae, Rhynchites heros;*

(c) pest belonging to the Bostrichidae family, for example, *Lyctus brunneus;*

(d) pest belonging to the Brentidae family, for example, *Cylas fonnicarius;*

(e) pest belonging to the Buprestidae family, for example, *Agrilus sinuatus;*

(f) pest belonging to the Cerambycidae family, for example, *Anoplophora malasiaca, Monochamus alternatus, Psacothea hilaris, Xylotrechus pyrrhoderus;*

(g) pest belonging to the Chrysomelidac family, for example, *Bruchus pisorum* and *Bruchus rufimanus* of *Bruchus* spp.; for example, *Diabrotica barberi, Diabrotica undecimpunctata* and *Diabrotica virgifera* of *Diabrotica* spp.; for example, *Phyllotreta nemorum* and *Phyllotreta striolata* of *Phyllotreta* spp.; others such as *Aulacophora femoralis, Callosobruchus chinensis, Cassida nebulosa, Chaetocnema concinna, Leptinotarsa decemlineata, Oulema oryzae, Psylliodes angusticollis;*

(h) pest belonging to the Coccinellidae family, for example, *Epilachna varivestis* and *Epilachna vigintioctopunctata* of *Epilachna* spp.;

(i) pest belonging to the Curculionidae family, for example, *Anthonomus grandis* and *Anthonomus pomorum* of *Anthonomus* spp.; for example, *Sitophilus granaries* and *Sitophilus zeamais* of *Sitophilus* spp.; others such as *Echinocnemus squameus, Euscepes postfasciatus, Hylobius abietis, Hypera postica, Lissohoptrus oryzophilus, Otiorhynchus sulcatus, Sitona lineatus, Sphenophorus venatus;*

(j) pest belonging to the Elateridae family, for example, *Melanotus fortnumi* and *Melanotus tamsuyensis* of *Melanotus* spp.;

(k) pest belonging to the Nitidulidae family, for example, *Epuraea domina;*

(l) pest belonging to the Scarabaeidae family, for example, *Anomala cuprea* and *Anomala rufocuprea* of *Anomala* spp.; others such as *Cetonia aurata, Gametis jucunda, Heptophylla picea, Melolontha melolontha, Popillia japonica;*

(m) pest belonging to the Scolytidae family, for example, *Ips typographus;*

(n) pest belonging to the Staphylinidae family, for example, *Paederus fuscipes;*

(o) pest belonging to the Tenebrionidae family, for example, *Tenebrio molitor, Tribolium castaneum;*

(p) pest belonging to the Trogossitidae family, for example, *Tenebroides mauritanicus.*

(5) Pest of Diptera Order (A) Brachycera Suborder (a) pest belonging to the Agromyzidae family, for example, *Liriomyza bryoniae, Liriomyza chinensis, Liriomyza sativae* and *Liriomyza trifolii* of *Liriomyza* spp.; others such as *Chromatomyia horticola, Agromyza oryzae;*

(b) pest belonging to the Anthomyiidae family, for example, *Delia platura, Delia radicum* of *Delia* spp.; others such as *Pegomya cunicularia;*

(c) pest belonging to the Drosophilidae family, for example, *Drosophila melanogaster* and *Drosophila suzukii* of *Drosophila* spp.;

(d) pest belonging to the Ephydridae family, for example, *Hydrellia griseola;*

(e) pest belonging to the Psilidae family, for example, *Psila rosae;*

(f) pest belonging to the Tephritidae family, for example, *Bactrocera cucurbitae* and *Bactrocera dorsalis* of *Bactrocera* spp.; for example, *Rhagoletis cerasi* and *Rhagoletis pomonella* of *Rhagoletis* spp.; others such as *Ceratitis capita, Dacus oleae.*

(B) Nematocera Suborder (a) pest belonging to the Cecidomyiidae family, for example, *Asphondylia yushimai, Contarinia sorghicola, Mayetiola destructor, Sitodiplosis mosellana.*

(6) Pest of Orthoptera Order (a) pest belonging to the Acrididae family, for example, *Schistocerca Americana* and *Schistocerca gregaria* of *Schistocerca* spp.; others such as *Chortoicetes terminifera, Dociostaurus maroccanus, Locusta migratoria, Locustana pardalina, Nomadacris septemfasciata, Oxya yezoensis;*

(b) pest belonging to the Gryllidae family, for example, *Acheta domestica, Teleogryllus emma;*

(c) pest belonging to the Gryllotalpidae family, for example, *Gryllotalpa orientalis;*

(d) pest belonging to the Tettigoniidae family, for example, *Tachycines asynamorus.*

(7) Acari (A) Acaridida of Astigmata Order:

(a) acari belonging to the Acaridae family, for example, *Rhizoglyphus echinopus* and *Rhizoglyphus robini* of *Rhizoglyphus* spp.; *Tyrophagus neiswanderi, Tyrophagus perniciosus, Tyrophagus putrescentiae* and *Tyrophagus similis* of *Tyrophagus* spp.; and others such as *Acarus siro, Aleuroglyphus ovatus, Mycetoglyphus fungivorus;*

(B) Actinedida of Prostigmata Order (a) acari belonging to the Tetranychidae family, for example, *Bryobia praetiosa* and *Bryobia rubrioculus* of *Bryobia* spp.; for example, *Eotetranychus asiaticus, Eotetranychus boreus, Eotetranychus celtis, Eotetranychus geniculatus, Eotetranychus kankitus, Eotetranychus pruni, Eotetranychus shii, Eotetranychus smithi, Eotetranychus suginamensis* and *Eotetranychus uncatus* of *Eotetranychus* spp.; for example, *Oligonychus hondoensis, Oligonychus ilicis, Oligonychus karamatus, Oligonychus mangiferus, Oligonychus orthius, Oligonychus perseae, ligonychus pustulosus, Oligonychus shinkajii* and *Oligonychus ununguis* of *Oligonychus* spp.; for example, *Panonychus citri, Panonychus mori* and *Panonychus uhni* of *Panonychus* spp.; for example, *Tetranychus cinnabarinus, Tetranychus kanzawai, Tetranychus ludeni, Tetranychus quercivorus, Tetranychus phaselus, Tetranychus urticae* and *Tetranychus viennensis* of *Tetranychus* spp.; for example, *Aponychus corpuzae* and *Aponychus firmianae* of *Aponychus* spp.; for example, *Sasanychus akitanus* and *Sasanychus pusillus* of *Sasanychus* spp.; for example, *Shizotetranychus celarius, Shizotetranychus longus, Shizotetranychus miscanthi, Shizotetranychus recki* and *Shizotetranychus schizopus* of *Shizotetranychus* spp.; others such as *Tetranychina hardi, Tuckerella pavonifoimis, Yezonychus sapporensis*;

(b) acari belonging to the Tenuipalpidae family, for example, *Brevipalpus lewisi, Brevipalpus obovatus, Brevipalpus phoenicis* and *Brevipalpus russulus* of *Brevipalpus* spp.; for example, *Tenuipalpus pacificus* and *Tenuipalpus zhizhilashviliae* of *Tenuipalpus* spp.; and others such as *Dolichotetranychus floridanus*;

(c) acari belonging to the Eriophyidae family, for example, *Aceria diospyri, Aceria ficus, Aceria japonica, Aceria kuko, Aceria paradianthi, Aceria tiyingi, Aceria tulipae* and *Aceria zoysiea* of *Aceria* spp.; for example, *Eriophyes chibaensis* and *Eriophyes emarginatae* of *Eriophyes* spp.; for example, *Aculops lycopersici* and *Aculops pelekassi* of *Aculops* spp.; for example, *Aculus fockeui, Aculus schlechtendali*, which belong *Aculus* spp.; and others such as *Acaphylla theavagrans, Calacarus carinatus, Colomerus vitis, Calepitrimerus vitis, Epitrimerus pyri, Paraphytoptus kikus, Paracalacarus podocarpi, Phyllocotruta citri*;

(d) acari belonging to the Transonemidae family, for example, *Tarsonemus bilobatus* and *Tarsonemus waitei* of *Tarsonemus* spp.; others such as *Phytonemus pallidus, Polyphagotarsonemus latus*;

(e) acari belonging to the Penthaleidae family, for example, *Penthaleus erythrocephalus* and *Penthaleus major* of *Penthaleus* spp.;

The harmful organism control agent, insecticide or acaricide of the present invention may include an additional ingredient other than the diarylimidazole compound. Examples of the additional ingredient include well-known carriers for formulation. In addition, well-known bactericides, insecticides/acaricides, nematocides, soil pesticides, plant regulators, synergists, fertilizers, soil improvers, animal feeds and the like may also be exemplified as the additional ingredient. By adding these additional ingredients, synergistic effects can be exhibited.

Examples of the insecticides/acaricides, nematocides, soil pesticides, anthelmintic agents and the like are as follow.

(1) Acetylcholine esterase inhibitor:

(a) Carbamate-based: alanycarb, aldicarb, bendiocarb, benfuracarb, butocarboxim, butoxycarboxim, carbaryl, carbofuran, carbosulfan, ethiofencarb, fenobucarb, foinuetanate, furathiocarb, isoprocarb, methiocarb, methomyl, oxamyl, pirimicarb, propoxur, thiodicarb, thiofanox, triazamate, trimethacarb, XMC, xylycarb; fenothiocarb, MIPC, MPMC, MTMC, aldoxycarb, allyxycarb, aminocarb, bufencarb, cloethocarb, metam-sodium, promecarb;

(b) Organic phosphorus-based: acephate, azamethiphos, azinphos-ethyl, azinphos-methyl, cadusafos, chlorethoxyfos, chlorfenvinphos, chlormephos, chlorpyrifos, chlorpyriphos-methyl, coumaphos, cyanophos, demeton-S-methyl, diazinon, dichlorvos/DDVP, dicrotophos, dimethoate, dimethylvinfos, disulfoton, EPN, ethion, ethoprophos, famphur, fenamiphos, fenitrothi on, fenthion, fosthiazete, heptenophos, imicyafos, isofenphos, isocarbophos, isoxathion, malathion, mecarbam, methamidophos, methidathion, mevinphos, monocrotophos, naled, omethoate, oxydemeton-metyl, parathion, parathion-methyl, phenthoate, phorate, phosalone, phosmet, phosphamidon, phoxim, pirimiphos-methyl, profenofos, propetamphos, prothiofos, pyraclofos, pyridafenthion, quinalphos, sulfotep, tebupirimfos, temephos, terbufos, tetrachlorvinphos, thiomethon, triazophos, trichlorfon, vamidothion; bromophos-ethyl, BRP, carbophenothion, cyanofenphos, CYAP, demeton-S-methyl sulphone, dialifos, dichlofenthion, dioxabenzofos, etrimfos, fensulfothion, flupyrazofos, fonofos, formothion, fosmethilan, isazophos, iodofenphos, methacrifos, pirimiphos-ethyl, phosphocarb, propaphos, prothoate, sulprofos.

(2) GABA-agonistic chloride ion channel antagonist: chlordane, endosulfan, ethiprole, fipronil, pyrafluprole, pyriprole; camphechlore, heptachlor, dienochlor.

(3) Sodium channel modulator: acrinathrin, d-cis-trans-allethrin, d-trans allethrin, bifenthrin, bioallethrin, bioallethrin S-cyclopentyl isomer, bioresmethrin, cycloprotophosphorus, cycloprothrin, cyfluthrin, β-cyfluthrin, cyhalothrin, λ-cyhalothrin, γ-cyhalothrin, cypermethrin, α-cypermethrin, β-cypermethrin, θ-cypermethrin, ζ-cypettnethrin, cyphenothrin [(1R)-trans isomer], δ-methrin, empenthrin [(EZ)-(1R)-isomer], esfenvalerate, ethofenprox, fenpropathrin, fenvalerate, flucythrinate, flumethrin, tau-fluvalinate, halfenprox, imiprothrin, kadethrin, permethrin, phenothrin [(1R)-trans isomer], prallethrin, pyrethrum, resmethrin, silafluofen, tefluthrin, tetramethrin, tetramethrin [(1R)-isomer], tralomethrin, transfluthrin; allethrin, pyrethrin, pyrethrin I, pyrethrin II, profluthrin, dimefluthrin, bioethanomethrin, biopeimethrin, transpermethirn, fenfluthrin, fenpirithrin, flubrocythrinate, flufenoprox, metofluthrin, protrifenbute, pyresmethrin, terallethrin.

(4) Nicotinic acetylcholine receptor agonist: acetamiprid, clothianidine, dinotefuran, imidacloprid, nitenpyram, nithiazine, thiacloprid, thiamethoxam, sulfoxaflor, nicotine, flupyradifurone.

(5) Nicotinic acetylcholine receptor allosteric modulator: spinetoram, spinosad.

(6) Chloride channel activator: abamectin, emamectin benzoate, lepimectin, milbemectin; ivermectin, seramectin, doramectin, eprinomectin, moxidectin; milbemycin; milbemycin oxime.

(7) Juvenile hormone-like substances: hydroprene, kinoprene, methoprene, fenoxycarb, pyriproxyfen, diofenolan, epofeneonane, triprene.

(8) Other nonspecific inhibitor: methyl bromide, chloropicrin, sulfuryl fluoride, borax, tartar emetic.

(9) Homoptera selective feeding inhibitor: flonicamid, pymetrozine, pyrifluquinazon.

(10) Acari growth inhibitor: clofentezine, diflovidazin, hexythiazox, etoxazole.

(11) Microorganism-derived insect midgut inner membrane distrupting agent: *Bacillus thuringiensis* subsp. Israelensi, *Bacillus sphaericus, Bacillus thuringiensis* subsp. Aizawai, *Bacillus thuringiensis* subsp. Kurstaki, *Bacillus thuringiensis* subsp. Tenebrionis, Bt crop protein: Cry1Ab, Cry1Ac, Cry1Fa, Cry1A.105, Cry2Ab, Vip3A, mCry3A, Cry3Ab, Cry3Bb, Cry34Ab1/Cry35Ab1.

(12) Mitochondria ATP biosynthesis enzyme inhibitor: diafenthiuron, azocyclotin, eyhexitin, fenbutatin oxide, propargite, tetradifon.

(13) Oxidative phosphorylation uncoupling agent: chlorfenapyr, sulfluramid, DNOC; binapacryl, dinobuton, dinocap.

(14) Nicotinic acetylcholine receptor channel blocker: bensultap, cartap hydrochloride; nereistoxin; thiosultap-sodium, thiocyclarm.

(15) Chitin synthesis inhibitor: bistrifluron, chlorfluazuron, diflubenzuron, flucycloxuron, flufenoxuron, hexaflumuron, lufenuron, novaluron, nobifumuron, teflubenzuron, triflumuron, buprofezin, fluazuron.

(16) Diptera molting disturbing agent: cyromazine.

(17) Molting hotmone receptor agonist: chromafenozide, halofenozide, methoxyfenozide, tebufenozide.

(18) Octopamine receptor agonist: amitraz, demiditraz, chlordimeform.

(19) Mitochondria electron transfer chain complex III inhibitor: acequinocyl, fluacrypyrim, hydramethylnon.

(20) Mitochondria electron transfer chain complex I inhibitor: fenazaquin, fenproximate, pyrimidifen, pyridaben, tebufenpyrad, tolfenpyrad, rotenone.

(21) Voltage-dependent sodium channel blocker: indoxacarb, metaflumizone.

(22) Acetyl CoA carboxylase inhibitor: spirodiclofen, spiromesifen, spirotetramat.

(23) Mitochondria electron transfer chain complex IV inhibitor: aluminium phosphide, calcium phosphide, phosphine, zinc phosphide, cyanide.

(24) Mitochondria electron transfer chain complex II inhibitor: cyenopyrafen, cyflumetofen, pyflubumide.

(25) Ryanodine receptor modulator: chlorantraniliprole, cyantraniliprole, flubendiamide, cyclaniliprole, tetraniliprole.

(26) Mixed function oxidase inhibitor compound: piperonyl butoxide.

(27) Latrophilin receptor agonist: depsipeptide, cyclodepsipeptide, 24 membered cyclodepsipeptide, emodepside.

(28) Others (action mechanism is unknown): azadirachtin, benzoximate, bifenazate, bromopropylate, quinomethionate, cryolite, dicofol, pyridalyl; benclothiaz, sulfur, amidoflumet, 1,3-dichloropropene, DCIP, phenisobromolate, benzomate, methaldehyde, chlorobenzilate, chlothiazoben, dicyclanil, fenoxacrim, fentrifanil, flubenzimine, fluphenazine, gossyplure, japonilure, metoxadiazone, oil, potassium oleate, tetrasul; triarathene; afidopyropen, flometoquin, flufiprole, fluensulfone, meperfluthrin, tetramethylfluthrin, tralopyril, dimefluthrin, methylneodecanamide; fluralaner, afoxolaner, fluxametamide,
5-[5-(3,5-dichlorophenyl)-5-trifluoromethyl-4,5-dihydroisoxazole-3-yl]-2-(1H-1,2,4-triaz ole-1-yl)benzonitrile (CAS:943137-49-3), broflanilide, other meta-diamide type.

(29) Antiparastic agent:
(a) benzimidazoles: fenbendazole, albendazole, triclabendazole, oxibendazole, mebendazole, oxfendazole, parbendazole, flubendazole; febantel, netobimin, thiophanate; thiabendazole, cambendazole;
(b) salicylanilides: closantel, oxyclozanide, rafoxanide, niclosamide;
(c) substituted phenols: nitroxinil, nitroscanate;
(d) pyridines: pyrantel, morantel;
(e) imidazothiazoles: levamisole, tetramisole;
(f) tetrahydropyrimidines: praziquantel, epsiprantel;
(g) other antiparastic agents: cyclodien, riania, clorsulon, metronidazole, demijitorazu; piperazine, diethyl carbamazine, dichlorophen, monepantel, tribendimidine, amidantel; thiacetarsamide, melorsamine, arsenamide.

Specific examples of the bactericide are as follows.
(1) Nucleic acid biosynthesis inhibitor:
(a) RNA polymerase I inhibitor: benalaxyl, benalaxyl-M, furalaxyl, metalaxyl, metalaxyl-M, oxadixyl; clozylacon, ofurace;
(b) adenosine deaminase inhibitor: bupirimate, dimethirimol, ethirimol;
(c) DNA/RNA synthesis inhibitor: hymexazol, octhilinone;
(d) DNA topoisomerase II inhibitor: oxophosphoric acid;
(2) Karyokinesis inhibitor and cell division inhibitor:
(a) β-tubulin polymerization inhibitor: benomyl, carbendazim, chlorfenazole, fuberidazole, thiabendazole; thiophanate, thiophanate-methyl; diethofencarb; zoxamide; ethaboxam;
(b) cell division inhibitor: pencycuron;
(c) delocalization inhibitor of spectrin-like protein: fluopicolide;
(3) Respiration inhibitor:
(a) complex I NADH oxidation-reduction inhibitor: diflumetorim; tolfenpyrad;
(b) complex II succinic acid dehydrogenase inhibitor: benodanil, flutolanil, mepronil; isofetamido, fluopyram; fenfuram, furmecyclox; carboxin, oxycarboxin; thifluzamide; benzovindiflupyr, bixafen, fluxapyroxad, furametpyr, isopyrazam, penflufen, penthiopyrad, Sedaxan; boscalid;
(c) complex III ubiquinol oxidase Qo inhibitor: azoxystrobin, coumoxystrobin, coumethoxystrobin, enoxastrobin, flufenoxystrobin, picoxystrobin, pyraoxystrobin; pyraclostrobin, pyrametostrobin, triclopyricarb; kresoximmethyl, trifloxystrobin; dimoxystrobin, fenaminstrobin, metominostrobin, orysastrobin; famoxadone; fluoxastrobin; fenamidone; pyribencarb;
(d) complex III ubiquinol reductase Qi inhibitor: cyazofamid; amisulbrom;
(e) oxidative phosphorylation uncoupling agent: binapacryl, meptyldinocap, dinocap; fluazinam; ferimzone;
(f) oxidative phosphorylation inhibitor (ATP synthase inhibitor): fenthin acetate, fentin chloride, fentin hydroxide;
(g) ATP production inhibitor: silthiofam;
(h) complex III cytochrome bc1 (ubiquinone reductase) Qx (unknown) inhibitor: ametoctradin;
(4) Amino acid and protein synthesis inhibitor
(a) methionine biosynthesis inhibitor: andoprim, cyprodinil, mepanipyrim, pyrimethanil;
(b) protein synthesis inhibitor: blasticidin-S; kasugamycin; kasugamycin hydrochloride; streptomycin; oxytetracycline.
(5) Signal transfer inhibitor:
(a) quinoxyfen, proquinazid;
(b) MAP/histidine kinase inhibitor in osmotic pressure signal transfer: fenpiconil, fludioxonil; chlozolimate, iprodione, procymidone, vinclozolin;
(6) Lipid and cell membrane synthesis inhibitor:
(a) phospholipid biosynthesis and methyltransferase inhibitor: edifenphos, iprobenfos, pyrazophos; isoprothiolane;
(b) lipid peroxide agent: biphenyl, chloroneb, dichloran, quintozene, tecnazene, tolclofos-methyl; etridiazole;
(c) agents affecting cell membrane: iodocarb, propamocarb, propamocarb hydrochloride, propamocarb-fosetylate, prothiocarb;
(d) microorganisms disturbing virus cell membrane: *bacillus subtilis, bacillus subtilis* strain QST713, *bacillus subtilis* strain FZB24, *bacillus subtilis* strain MBI600, *bacillus subtilis* strain D747;
(e) agents disturbing cell membrane: *melaleuca alternifolia* (tea tree) extract.
(7) Cell membrane sterol biosynthesis inhibitor:
(a) C14 position demethylation inhibitor in sterol biosynthesis: triforine; pyrifenox, pyrisoxazole; fenarimol, flurprimidol, nuarimol; imazalil, imazalil-sulphate, oxpoconazole, pefurazoate, prochloraz, triflumizole, viniconazole; azaconazole, bitertanol, bromconazole, cyproconazole, diclobutrazol, difenoconazole, diniconazole, diniconazole-M, epoxyconazole, etaconazole, fenbuconazole, fluquinconazole, flusilazole, flutriafol, furconazole, furconazole-cis, hexaconazole, imibenconazole, ipuconazole, meteonazole, myclobutanil, penconazole, propiconazole, quinconazole, simeconazole, tebuconazole, tetraconazole, triadimefon, triadimenol, triticonazole; prothioconazole, voriconazole;

(b) Δ14 reductase and Δ8→Δ7-isomerase inhibitor in sterol biosynthesis: aldimorph, dodemorph, dodemorph-acetate, fenpropimorph, tridemorph, fenpropidine, piperalin; spiroxamine;

(c) 3-keto reductase inhibitor in C4 position demethylation in sterol biosynthesis system: fenhexamid; fenpyrazamine;

(d) squalene epoxidasc inhibitor in sterol biosynthesis system: pyributicarb; naftifen, terbinafine.

(8) Cell wall synthesis inhibitor
  (a) trehalase inhibitor: validamycin;
  (b) chitin synthetase inhibitor: polyoxins, polyoxorim;
  (c) cellulose synthetase inhibitor: dimethomorph, flumorph, pyrimorph; benthiavalicarb, iprovalicarb, tolprocarb, valifenalate; mandipropamide;

(9) Melanin biosynthesis inhibitor
  (a) reductase inhibitor in melamin biosynthesis: fthalide; pyroquilon; tricyclazole;
  (b) anhydrase inhibitor in melamin biosynthesis: carpropamid; diclocymet; fenoxanil;

(10) Resistance-inducing agent of host plant:
  (a) agents affecting salicylic acid synthetic pathway: acibenzolar-s-methyl;
  (b) others: probenazole; tiadinil; isotianil; laminarin; extract liquid of reynoutria sachalinensis.

(11) agents of which the activity is unknown: cymoxanil, osetyl.aluminum, phosphoric acid (phosphate), tecloftalam, triazoxide, flusulfamide, diclomezine, methasulfocarb, cyflufenamid, metrafenone, pyriofenone, dodine, dodine free base, flutianil.

(12) Agent having multy activities: copper (copper salt), bordeaux mixture, copper hydroxide, copper naphthalate, copper oxide, oxychloride copper, copper sulfate, sulfur, sulfur product, calcium polysulfide; ferbam, mancozeb, maneb, mancopper, metiram, polycarbamate, propineb, thiram, zineb, ziram; captan, captafol, folpet; chlorothalonil; dichlofluanid, tolylfluanid; guazatine, iminoctadine acetate, iminoctadine albesilate; anilazine; dithianon; chinomethionat; fluoroimide.

(13) Other agents: DBEDC, fluor folpet, guazatine acetate, bis (8-quinolinolato) copper (II), propamidine, chloropicrin, cyprofuram, agrobacterium, bethoxazin, diphenylamine, methyl isothiocyanate (MITC), mildew-mycin, capsaicin, curfraneb, cyprosulfamide, dazomet, debacarb, dichlorophen, difenzoquat, difenzoquat.methyl sulfonate, flumetover, fosetyl.calcium, fosetyl.sodium, irmamycin, natamycin, nitrothal isopropyl, oxamocarb, puropamocin sodium, pyrrolnitrin, tebufloquin, tolnifanide, zarilamide, algophase, amicarthiazol, oxathiapiprolin, metiram zinc, benthiazole, trichlaamide, uniconazole, mildew-mycin, oxyfenthiin, picarbutrazox.

Furthermore, specific examples of the plant growth regulators are as follows.

abscisic acid, kinetin, benzylaminopurine, 1,3-diphenylurea, forchlorfenuron, thidiazuron, chlorfenuron, dihydrozeatin, gibberellins A, gibberelline A4, gibberelline A7, gibberelline A3, 1-methylcyclopropene, N-acetyl aminoethoxyvinyl glycine (aviglycine), aminooxyacetate, silver nitrate, cobalt chloride, IAA, 4-CPA, cloprop, 2,4-D, MCPB, indole-3-butyrate, dichlorprop, phenothiol, 1-naphthyl acetamide, ethychlozate, cloxyfonac, maleic acid hydrazide, 2,3,5-triiodobenzoic acid, salicylic acid, salicylate, (−)-jasmonic acid, methyl jasmonate, (+)-strigol, (+)-deoxystrigol, (+)-orobanchol, (+)-sorgolactone, 4-oxo-4-(2-phenyl ethyl)aminobutyric acid; ethephon, chloimequat, mepiquat chloride, benzyl adenine, 5-amino levulinic acid.

[External Parasite Control Agent]

The eternal parasite control agent of the present invention includes at least one of the diarylimidazole compound of the present invention as an active ingredient. The diarylimidazole compound of the present invention has superior effect for preventing the external parasites that are harmful for humans and animals.

Examples of the external parasite include acari, louse, flea, mosquito, biting housefly, flesh fly and the like.

Examples of the host animals to be treated by the external parasite control agent of the present invention include warm-blooded animals such as pet animals for example, dogs, cats or the like; pet birds; domestic animals for example, cows, horses, pigs, sheep or the like; domestic fowl; and the like. In addition, honeybees, stag beetles may also be exemplified.

The external parasites live on the host animals, especially live inside or upon the warm-blooded animals. More specifically, the external parasites are parasitic in the back, armpit, underbelly, inner thigh and the like of the host animals and obtain nutritional sources such as blood, dandruff from the animals to live.

The external parasite control agent of the present invention can be applied by a known veterinary method (topical, oral, parenteral or subcutaneous administration). Examples of the method include orally administering tablets, capsules and foods mixed with the external parasite control agent to the animals; administering to the animals by using immersion liquid, suppository or injection (intramuscular, subcutaneous, intravenous, intraabdominal or the like); topically administering oily or aqueous liquid preparation by spraying, pouring on, spotting on or the like; topically administering by attaching a collar, ear tag or the like made by molding a mixture obtained by kneading the external parasite control agent with a resin to the animals; and the like.

Specifica examples of the external parasite able to be prevented are as follows.

(1) Acari

Acari belonging to the Dermanyssidae family, acari belonging to the Macronyssidae family, acari belonging to the Laelapidae family, acari belonging to the Varroidae family, acari belonging to the Argasidae family, acari belonging to the Ixodidae family, acari belonging to the Psoroptidae family, acari belonging to the Sarcoptidae family, acari belonging to the Knemidokoptidae family, acari belonging to the Demodixidae family, acari belonging to the Trombiculidae family, insect-parasitic acari such as *Coleopterophagus berlesei* or the like.

(2) Phthiraptera Order

Louse belonging to the Haematopinidae family, louse belonging to the Linognathidae family, biting louse belonging to the Menoponidae family, biting louse belonging to the Philopteridae family, biting louse belonging to the Trichodectidae family;

(3) Siphonaptera Order

Flea belonging to the Pulicidae family, for example, *Ctenocephalides canis* and *Ctenocephalides felis* of *Ctenocephalides* spp.;

Flea belonging to the Tungidae family, flea belonging to the Ceratophyllidae family, flea belonging to the Leptopsyllidae family;

(4) Hemiptera Order
(5) Harmful Organism of Diptera Order

Mosquito belonging to the Culicidae family, black fly belonging to the Simuliidae family, punkie belonging to the Ceratopogonidae family, fly belonging to the Tabanidae family, fly belonging to the Muscidae family, *glossina* belonging to the Glossinidae family; flesh fly belonging to the Sarcophagidae family, fly belonging to the Hippoboscidae family, fly belonging to the Calliphoridae family, fly belonging to the Oestridae family;

[Internal Parasite Control Agent or Expellent]

The internal parasite control agent or expellent of the present invention include at least one selected from the diarylimidazole compound of the present invention as an active ingredient.

The parasites to be prevented by the internal parasite control agent or expellent of the present invention live in host animals, especially live inside of the worm-blooded animals or fishes (internal parasite). Examples of the host animals for which the parasite control agent or expellent of the present invention is applicable include worm-blooded animals such as humans, domestic mammals (for example, cows, horses, pigs, sheep, goats or the like), experimental animals (for example, mice, rats, merines unduiculatus or the like), pet animals (for example, hamsters, guinea pigs, dogs, cats, horses, squirrels, rabbits, ferrets or the like), wild animals and zoo mammals (for example, monkeys, foxes, deer, buffalos or the like), domestic fowl (for example, turkeys, ducks, chickens, qualil or the like), pet birds (for example, pigeon, parrot, magpie, java sparrow, parakeet, bengalee, canary or the like); fishes such as salmon, trout, Koi or the like; and the like. By preventing or extetininating the parasites, parasitic disease carried by parasites can be prevented or treated.

Examples of the parasites to be prevented or exterminated are as follows.

(1) Nematode of Enoplida Order (a) *Dioctophyma renale* belonging to the Dioctophymatidae family, for example, *Dioctophyma renale* of *Dioctophyma* spp.;

(b) *Dioctophyma renale* belonging to the Soboliphymatidae family, for example, *Soboliphyme abei* and *Soboliphyme baturini* of *Soboliphyme* spp.;

(2) Nematode of Enoplida Order (a) *Trichinella spiralis* belonging to the Trichinellidae family, for example, *Trichinella spiralis* of *Trichinella* spp.;

(b) whipworms belonging to the Trichuridae family, for example, *Capillaria annulata*, *Capillaria contorta*, *Capillaria hepatica*, *Capillaria perforans*, *Capillaria plica* and *Capillaria suis* of *Capillaria* spp.; *Trichuris vulpis*, *Trichuris discolor*, *Trichuris ovis*, *Trichuris skrjabini* and *Trichuris suis* of *Trichuris* spp.;

(3) Nematode of Rhabditida Order

*Strongyloides stercoralis* belonging to the Strongyloididae family, for example, *Strongyloides papillosus*, *Strongyloides planiceps*, *Strongyloides ransomi*, *Strongyloides suis*, *Strongyloides stercoralis*, *Strongyloides tumefaciens* and *Strongyloides ratti* of *Strongyloides* spp.;

(4) Nematode of Strongylida Order

Hookworm belonging to the Ancylostomatidae family, for example, *Ancylostoma braziliense*, *Ancylostoma caninum*, *Ancylostoma duodenale* and *Ancylostoma tubaeforme* of *Ancylostoma* spp.; *Uncinaria stenocephala* of *Uncinaria* spp.; *Bunostomum phlebotomum* and *Bunostomum trigonocephalum* of *Bunostomum* spp.;

(5) Nematode of Strongylida Order (a) Nematode belonging to the Angiostrongylidae family, for example, *Aelurostrongylus abstrusus* of *Aelurostrongylus* spp.; *Angiostrongylus vasorum* and *Angiostrongylus cantonesis* of *Angiostrongylus* spp.;

(b) Nematode belonging to the Crenosomatidae family, for example, *Crenosoma aerophila* and *Crenosoma vulpis* of *Crenosoma* spp.;

(c) Nematode belonging to the Filaroididae family, for example, *Filaroides hirthi* and *Filaroides osleri* of *Filaroides* spp.;

(d) Lung worms belonging to the Metastrongylidae family, for example, *Metastrongylus apri*, *Metastrongylus asymmetricus*, *Metastrongylus pudendotectus* and *Metastrongylus salmi* of *Metastrongylus* spp.;

(e) Gapeworms trachea belonging to the Syngamidae family, for example, *Cyathostoma bronchialis* of *Cyathostoma* spp.; *Syngamus skrjabinomorpha* and *Syngamus trachea* of *Syngamus* spp.;

(6) Nematode of Strongylida Order (a) Nematode belonging to the Molineidae family, for example, *Nematodirus filicollis* and *Nematodirus spathiger* of *Nematodirus* spp.;

(b) Nematode belonging to the Dictyocaulidae family, for example, *Dictyocaulus filarial* and *Dictyocaulus viviparous* of *Dictyocaulus* spp.;

(c) Nematode belonging to the Haemonchidae family, for example, *Haemonchus contortus* of *Haemonchus* spp.; *Mecistocirrus digitatus* of *Mecistocirrus* spp.;

(d) Nematode belonging to the Haemonchidae family, for example, *Ostertagia ostertagi* of *Ostertagia* spp.;

(e) Nematode belonging to the Heligmonellidae family, for example, *Nippostrongylus braziliensis* of *Nippostrongylus* spp.;

(f) Nematode belonging to the Trichostrongylidae family, for example, *Trichostrongylus axei*, *Trichostrongylus colubriformis* and *Trichostrongylus tenuis* of *Trichostrongylus* spp.; *Hyostrongylus rubidus* of *Hyostrongylus* spp.; *Obeliscoides cuniculi* of *Obeliscoides* spp.;

(7) Nematode of Strongylida Order (a) Nematode belonging to the Chabertiidae family, for example, *Chabertia ovina* of *Chabertia* spp.; *Oesophagostomum brevicaudatum* (pig), *Oesophagostomum columbianum*, *Oesophagostomum dentatum*, *Oesophagostomum georgianum* (pig), *Oesophagostomum maplestonei*, *Oesophagostomum quadrispinulatum* (pig), *Oesophagostomum radiatum*, *Oesophagostomum venulosum* and *Oesophagostomum watanabei* of *Oesophagostomum* spp.;

(b) Nematode belonging to the Stephanuridae family, for example, *Stephanurus dentatus* of *Stephanurus* spp.;

(c) Nematode belonging to the Strongylidae family, for example, *Strongylus asini*, *Strongylus edentates*, *Strongylus equinus* and *Strongylus vulgaris* of *Strongylus* spp.;

(8) Nematode of the Oxyurida Order

Nematode belonging to the Oxyuridae family, for example, *Enterobius anthropopitheci* and *Enterobius vermicularis* of *Enterobius* spp.; *Oxyuris equi* of *Oxyuris* spp.; *Passalurus ambiguous* of *Passalurus* spp.;

(9) Nematode of Ascaridida Order (a) Nematode belonging to the Ascaridiidae family, for example, *Ascaridia galli* of *Ascaridia* spp.;

(b) Nematode belonging to the Heterakidae family, for example, *Heterakis beramporia*, *Heterakis brevispiculum*, *Heterakis gallinarum*, *Heterakis pusilla* and *Heterakis putaustralis* of *Heterakis* spp.;

(c) Nematode belonging to the Anisakidae family, for example, *Anisakis simplex* of *Anisakis* spp.;

(d) Nematode belonging to the Ascarididae family, for example, *Ascaris lumbricoides* and *Ascaris suum* of *Ascaris* spp.; *Parascaris equorum* of *Parascaris* spp.;

(e) Nematode belonging to the Toxocaridae family, for example, *Toxocara canis*, *Toxocara leonine*, *Toxocarasuum*, *Toxocara vitulorum* and *Toxocara cati* of *Toxocara* spp.;

(10) Nematode of Spirurida Order (a) Nematode belonging to the Onchocercidae family, for example, *Brugia malayi*, *Brugia pahangi* and *Brugia patei* of *Brugia* spp.; *Dipetalonema reconditum* of *Dipetalonema* spp.; *Dirofilaria immitis* of *Dirofilaria* spp.; *Filaria oculi* of *Filaria* spp.; *Onchocerca cervicalis*, *Onchocerca gibsoni* and *Onchocerca gutturosa* of *Onchocerca* spp.;

(b) Nematode belonging to the Setariidae family, for example, *Setaria digitate*, *Setaria equine*, *Setaria labiatopapillosa* and *Setaria marshalli* of *Setaria* spp.; *Wuchereria bancrofti* of *Wuchereria* spp.;

(c) Nematode belonging to the Filariidae family, for example, *Parafilaria multipapillosa* of *Parafilaria* spp.; *Stephanofilaria assamensis*, *Stephanofilaria dedoesi*, *Stephanofilaria kaeli*, *Stephanofilaria okinawaensis* and *Stephanofilaria stilesi* of *Stephanofilaria* spp.;

(11) Nematode of Spirurida Order (a) Nematode belonging to the Gnathostomatidae family, for example, *Gnathostoma doloresi* and *Gnathostoma spinigerum* of *Gnathostoma* spp.;

(b) Nematode belonging to the Habronematidae family, for example, *Habronema majus*, *Habronema microstoma* and *Habronema muscae* of *Habronema* spp.; *Draschia megastoma* of *Draschia* spp.;

(c) Nematode belonging to the Physalopteridae family, for example, *Physaloptera canis*, *Physaloptera cesticillata*, *Physaloptera erdocyona*, *Physaloptera felidis*, *Physaloptera gemina*, *Physaloptera papilloradiata*, *Physaloptera praeputialis*, *Physaloptera pseudopraerutialis*, *Physaloptera rara*, *Physaloptera sibirica* and *Physaloptera vulpineus* of *Physaloptera* spp.;

(d) Nematode belonging to the Gongylonematidae family, for example, *Gongylonema pulchrum* of *Gongylonema* spp.;

(e) Nematode belonging to the Spirocercidae family, for example, *Ascarops strongylina* of *Ascarops* spp.;

(f) Nematode belonging to the Thelaziidae family, for example, *Thelazia callipaeda*, *Thelazia gulosa*, *Thelazia lacrymalis*, *Thelazia rhodesi* and *Thelazia skrjabini* of *Thelazia* spp.;

[Control Agents Against Other Harmful Organisms]

Other than the above described harmful organisms, the harmful organism control agent of the present invention also has a superior effect for preventing the pests having a stinger or venom to damage humans and animals, pests carrying various pathogens and pathogenic bacteria, and pests giving unpleasant feelings to humans (toxic pest, hygienic pest, unpleasant pest).

Specific examples are as follows.

(1) Pests of Hymenoptera Order

Bees belonging to the Argidae family, bees belonging to the Cynipidae family, bees belonging to the Diprionidae family, alis belonging to the Formicidae family, bees belonging to the Mutillidae vamily family, bees belonging to the Vespidae family.

(2) Other Pests

Blattodea, termite, Araneae, centipede, millipede, crustacea, *Cimex lectularius*.

[Preparation Formulation]

Several examples of the harmful organism control agent, insecticide, acaricide, external parasite control agent, or internal parasite control agent or expellent of the present invention are shown bellow. However, the additives and the addition ratios are not limited to the examples and can be modified over a wide range. The term "part" in the preparation formulation indicates "part by weight".

The followings are the preparation formulations for agricultural and horticultural use and for paddy rice.

(Preparation 1: Wettable Powder)

40 parts of the diarylimidazole compound of the present invention, 53 parts of diatom earth, 4 parts of fatty alcohol sulfate and 3 parts of alkylnaphthalene sulfonate were uniformly mixed and finely pulverized to obtain a wettable powder including 40% of active ingredient.

(Preparation 2: Emulsion)

30 parts of the diarylimidazole compound of the present invention, 33 parts of xylene, 30 parts of dimethylformamide and 7 parts of polyoxyethylene alkylaryl ether were mixed and dissolved to obtain an emulsion including 30% of active ingredient.

(Preparation 3: Granules)

5 parts of the diarylimidazole compound of the present invention, 40 parts of talc, 38 parts of clay, 10 parts of bentonite and 7 parts of sodium alkylsulfate were uniformly mixed and crushed, followed by granulating into a granular shape having a diameter of 0.5 to 1.0 mm to obtain granules containing 5% active ingredient.

(Preparation 4: Granules)

5 parts of the diarylimidazole compound of the present invention, 73 parts of clay, 20 parts of bentonite, 1 part of sodium dioctyl sulfosuccinate and 1 part of potassium phosphate were thoroughly crushed and mixed followed by the addition of water, mixing well, granulating and drying to obtain granules containing 5% active ingredient.

(Preparation 5: Suspension)

10 parts of the diarylimidazole compound according to the present invention, 4 parts of polyoxyethylene alkyl allyl ether, 2 parts of sodium polycarboxylate, 10 parts of glycerin, 0.2 parts of xanthan gum and 73.8 parts of water were mixed and wet-crushed to a grain size of 3 microns or less to obtain a suspension containing 10% active ingredient.

The following are the preparation formulations of the external parasite control agent, or internal parasite control agent or expellent.

(Preparation 6: Granulated Powder)

5 part of the diarylimidazole compound of the present invention was dissolved in an organic solvent to obtain a solution, and sprayed the solution on 94 parts of kaolin and 1 part of white carbon, followed by evaporating the solvent under reduced pressure. This kind of granulated powder may be mixed with animal food.

(Preparation 7: Impregnating Agent)

0.1-1 parts of the diarylimidazole compound of the present invention and 99-99.9 parts of peanut oil were uniformly mixed, and then filter-sterilized by a sterilizing filter after adjustment.

(Preparation 8: Pour-on Agent)

5 parts of the diarylimidazole compound of the present invention, 10 parts of myristic acid ester and 85 parts of isopropanol were uniformly mixed to obtain a pour-on agent.

(Preparation 9: Spot-on Agent)

10-15 parts of the diarylimidazole compound of the present invention, 10 parts of palmitic acid ester and 75-80 parts of isopropanol were uniformly mixed to obtain a spot-on agent.

(Preparation 10: Spray-on Agent)

1 part of the diarylimidazole compound of the present invention, 10 parts of propylene glycol and 89 parts of isopropanol were uniformly mixed to obtain a spray-on agent.

EXAMPLES

The following provides Examples to explain the present invention more specifically. However, the present invention is not limited to the following examples.

Example 1

Synthesis of 2-(2-(ethylsulfonyl)-4-(trifluoromethyl)phenyl)-1-methyl-5-(4-(trifluoromethyl)phenyl)-1H-imidazole (Compound 1-3)

(Step 1)

Synthesis of 2-oxo-2-(4-(trifluoromethyl)phenyl)acetaldehyde oxime

[Chemical formula 9]

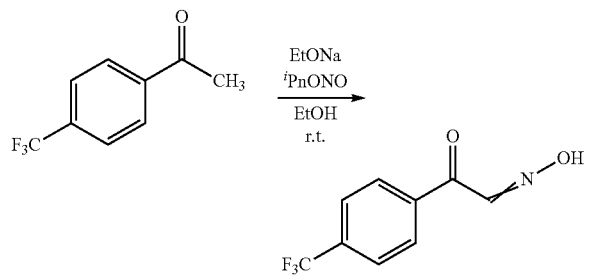

30 g (0.44 mol, 3.3 eq) of sodium ethoxide was dissolved in 700 mol of ethanol and cooled to 0° C. 25 g (0.13 mol, 1.0 eq) of p-(trifluoromethyl)acetophenone and 20 ml (d=0.87, 0.15 mmol, 1.1 eq) of isopentyl nitrite were added to the resulting solution, followed by stirring for 5 hours at room temperature. The resulting reaction liquid was then concentrated under reduced pressure and a saturated ammonium chloride aqueous solution was poured to the resulting residue. After that, the mixture was extracted with 20%-methanol/dichloromethane and the resulting organic layer was dried with anhydrous magnesium sulfate and filtered. The filtrate was concentrated under reduced pressure, and the residue was purified by silica gel column chromatography to obtain 15 g of the objective compound (yield: 51%).

$^1$H-NMR of the obtained compound is shown below:

$^1$H-NMR (400 MHz, CDCl$_3$): δ 8.45 (br s, 1H), 8.14 (m, 2H), 7.98 (s, 1H), 7.72 (m, 2H).

(Step 2)

Synthesis of 1-methyl-5-(4-(trifluoromethylphenyl)-1H-imidazole 3-oxide

[Chemical formula 10]

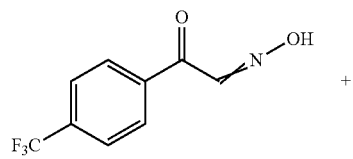

+

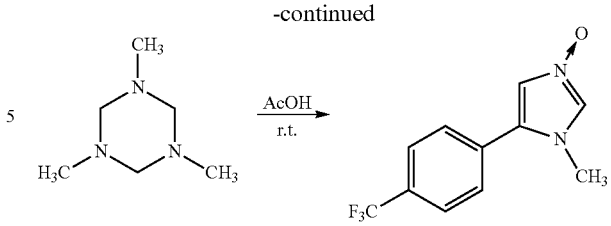

15 g (0.069 mol, 1.0 eq) of 2-oxo-2-(4-(trifluoromethyl)phenyl)acetaldoxime was dissolved in 300 ml of acetic acid followed by stirring at room temperature. 10 g (0.076 mol, 1.1 eq) of 1,3,5-trimethyl hexahydro-1,3,5-triazine was added to the resulting solution followed by stirring for 3 hours at room temperature. The resulting reaction liquid was then concentrated under reduced pressure and the obtained crude crystal was washed with 50%-ethyl acetate/normal hexane to obtain 11 g of the objected compound (yield: 66%).

$^1$H-NMR of the obtained compound is shown below:

$^1$H-NMR (400 MHz, CDCl$_3$): δ 8.14 (d, 1H), 7.75 (m, 2H), 7.50 (m, 2H), 7.30 (d, 1H), 3.66 (s, 3H).

(Step 3)

Synthesis of 2-(2-fluoro-4-(trifluoromethyl)phenyl)-1-methyl-5-(4-(trifluoromethyl)phenyl)-1H-imidazole 3-oxide (Compound 1-5)

[Chemical formula 11]

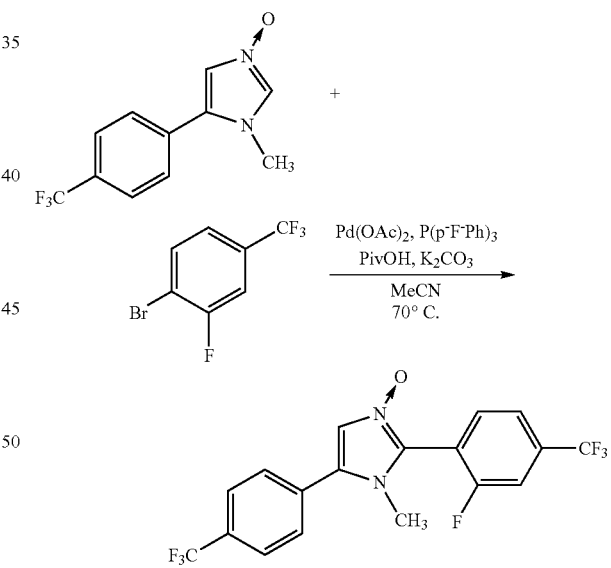

1.0 g (4.1 mmol, 1.1 eq) of 1-methyl-5-(4-(trifluoromethyl)phenyl)-1H-imidazole 3-oxide, 0.043 g (0.19 mmol, 5 mol %) of palladium acetate, 0.18 g (0.57 mol, 15 mol %) of tri(p-fluorophenyl)phosphine, 0.11 g (1.1 mmol, 30 mol %) of pivalic acid, and 1.0 g (7.4 mmol, 2.0 eq) of carbonic acid potassium were added to a reactor, followed by replacing the air with argon gas. 14 mol of anhydrous acetonitrile solution of 0.90 g (3.7 mmol, 1.0 eq) of 4-bromo-3-fluorobenzene trifluoride was added to the resulting mixture, followed by stirring over night at 70° C. The resulting reaction liquid was filtered over celite and concentrated under reduced pressure. The obtained crude crystal was washed with diethylether to obtain 1.1 g of the objective compound (yield: 73%).

¹H-NMR of the obtained compound is shown below:

¹H-NMR (400 MHz, CDCl₃): δ 8.21 (m, 1H), 7.80 (m, 2H), 7.64 (m, 1H), 7.59 (m, 2H), 7.57 (m, 1H), 7.47 (s, 1H), 3.57 (d, 3H).

(Step 4)

Synthesis of 2-(2-fluoro-4-(trifluoromethyl)phenyl)-1-methyl-5-(4-(trifluoromethyl)phenyl)-1H-imidazole (Compound 1-4)

[Chemicla formula 12]

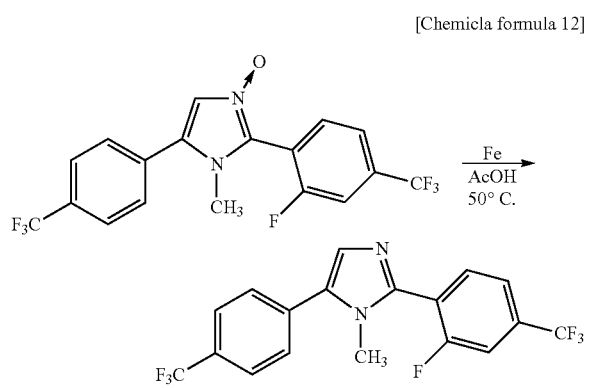

1.1 g (2.7 mmol, 1.0 eq) of 2-(2-fluoro-4-(trifluoromethyl)phenyl)-1-methyl-5-(4-(trifluoromethyl)phenyl)-1H-imidazole 3-oxide was dissolved in 30 ml of acetic acid followed by stirring at room temperature. 1.5 g (27 mmol, 10 eq) of electrolytic iron powder was then added to the resulting solution followed by stirring for 5 hours at 70° C. The resulting reaction liquid was concentrated under reduced pressure, neutralized by a saturated aqueous solution of sodium hydrogen carbonate, followed by filtering over celite. After that, the resulting mixture was extracted with dichloromethane and the obtained organic layer was dried by adding anhydrous magnesium sulfate and filtered. The filtrate was concentrated under reduced pressure to obtain 0.83 g of the objective compound (yield 83%).

¹H-NMR of the obtained compound is shown below:

¹H-NMR (400 MHz, CDCl₃): δ 7.84 (m, 1H), 7.74 (m, 2H), 7.61 (m, 1H), 7.58 (m, 1H), 7.51 (m, 1H), 7.35 (s, 1H), 3.61 (d, 3H).

(Step 5)

Synthesis of 2-(2-(ethylsulfanyl)-4-(trifluoromethyl)phenyl)-1-methyl-5-(4-(trifluoromethyl)phenyl)-1H-imidazole (Compound 1-7)

[Chemical formula 13]

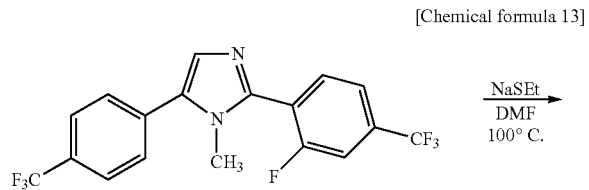

-continued

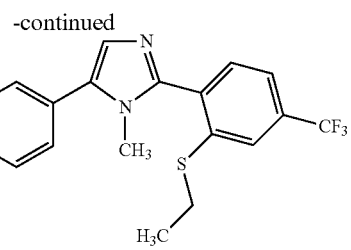

0.53 g (1.4 mmol, 1.0 eq) of 2-(2-fluoro-4-(trifluoromethyl)phenyl)-1-methyl-5-(4-(trifluoromethyl)phenyl)-1H-imidazole was dissolved in 14 ml of N,N-dimethyl formamide followed by stirring at room temperature. 0.72 g (80%, 6.8 mmol, 5.0 eq) of ethyl mercaptan sodium was then added to the resulting solution followed by stirring for 1 hour at 100° C. The resulting reaction liquid was cooled to room temperature followed by pouring water and extracted with ethyl acetate. The obtained organic layer was washed with brine, dried by adding anhydrous magnesium sulfate and filtered. The filtrate was concentrated under reduced pressure and the obtained residue was purified by silica gel column chromatography to obtain 0.30 g of the objective compound (yield: 50%).

¹H-NMR of the obtained compound is shown below:

¹H-NMR (400 MHz, CDCl₃): δ 7.73 (m, 2H), 7.60 (m, 3H), 7.53 (m, 2H), 7.33 (s, 1H), 3.52 (s, 3H), 2.94 (q, 2H), 1.32 (t, 3H).

(Step 6)

Synthesis of 2-(2-(ethylsulfonyl)-4-(trifluoromethyl)phenyl)-1-methyl-5-(4-(trifluoromethyl)phenyl)-1H-imidazole (Compound 1-3)

[Chemical 14]

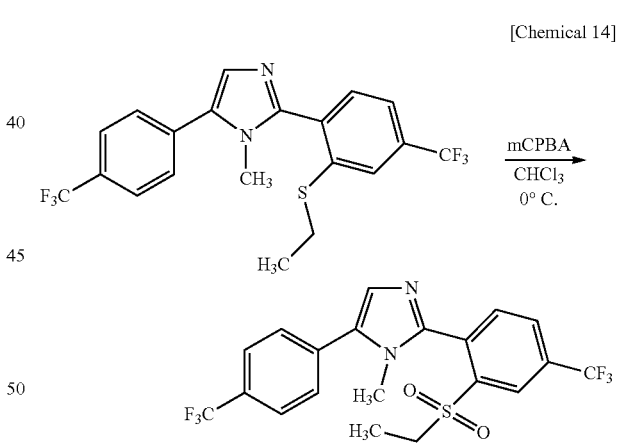

0.27 g (0.63 mmol, 1.0 eq) of 2-(2-ethyl sulfanyl-4-(trifluoromethyl)phenyl)-1-methyl-5-(4-(trifluoromethyl)phenyl)-1H-imidazol e was dissolved in 7 ml of chloroform followed by stirring at 0° C. 0.31 g (70%, 1.3 mmol, 2.0 eq) of metachloroperbenzoic acid was added to the resulting solution followed by stirring for 2 hours at 0° C. The resulting reaction liquid was poured to a mixed solution of saturated aqueous solution of sodium hydrogen carbonate and saturated aqueous solution of sodium thiosulfate followed by extracting with chloroform. The obtained organic layer was washed with brine, dried by adding anhydrous magnesium sulfate and filtered. The filtrate was concentrated under reduce pressure and the obtained residue was purified by silica gel column chromatography to obtain 0.15 g of the objective compound (yield: 51%).

$^1$H-NMR of the obtained compound is shown below:
$^1$H-NMR (400 MHz, CDCl$_3$): δ 8.47 (m, 1H), 8.03 (m, 1H), 7.73 (m, 3H), 7.60 (m, 2H), 3.47 (q, 2H), 3.44 (s, 3H), 1.26 (t, 3H).

TABLE 1 to TABLE 9 show the compounds of the present invention produced by the same production process of the above-described Examples. In addition, the physical properties of the compounds are shown in the column of "Physical Property". As the physical properties, property, melting point (m.p.) or refraction index are shown.

In addition, in the tables, Ph represents phenyl group, Me represents methyl group, Et represents ethyl group, $^n$Pr represents normal propyl group, $^i$Pr represents isopropyl group, $^c$Pr represents cyclopropyl group, nBu represent normal butyl group, sBu represents secondary butyl group and tBu represents tertial butyl group.

TABLE 1 shows the substituents of the compounds represented by formula (1).

[Chemical formula 15]

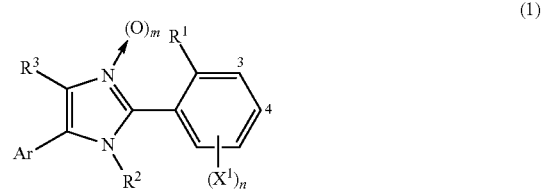

(1)

TABLE 1

| No. | R$^1$ | (X$^1$)n | Ar | R$^2$ | R$^3$ | m | Physical Property |
|---|---|---|---|---|---|---|---|
| 1-1 | SO$_2$Et | 4-CF$_3$ | 5-CF$_3$-pyridine-2-yl | Me | H | 0 | m.p. 145-148° C. |
| 1-2 | SEt | 4-CF$_3$ | 5-CF$_3$-pyridine-2-yl | Me | H | 0 | viscous oil |
| 1-3 | SO$_2$Et | 4-CF$_3$ | 4-CF$_3$—Ph | Me | H | 0 | m.p. 144-147° C. |
| 1-4 | F | 4-CF$_3$ | 4-CF$_3$—Ph | Me | H | 0 | m.p. 126-128° C. |
| 1-5 | F | 4-CF$_3$ | 4-CF$_3$—Ph | Me | H | 1 | m.p. 229-231° C. |
| 1-6 | SEt | 4-CF$_3$ | 4-CF$_3$—Ph | Me | Me | 0 | m.p. 96-101° C. |
| 1-7 | SEt | 4-CF$_3$ | 4-CF$_3$—Ph | Me | H | 0 | m.p. 111-113° C. |
| 1-8 | SEt | 4-CF$_3$ | 3-CF$_3$—Ph | Me | H | 0 | n$_D$(22.0° C.)1.5454 |
| 1-9 | SEt | 4-CF$_3$ | 2-CF$_3$—Ph | Me | H | 0 | viscous oil |
| 1-10 | SEt | — | 4-CF$_3$—Ph | Me | H | 1 | amorphous |
| 1-11 | SOEt | — | 4-CF$_3$—Ph | Me | H | 1 | m.p.: 194-195° C. |
| 1-12 | SO$_2$Et | — | 4-CF$_3$—Ph | Me | H | 1 | m.p.: 131-132° C. |
| 1-13 | SEt | — | 4-CF$_3$—Ph | Me | H | 0 | n$_D$(22.2° C.)1.5962 |
| 1-14 | SOEt | — | 4-CF$_3$—Ph | Me | H | 0 | m.p.: 162-164° C. |
| 1-15 | SO$_2$Et | — | 4-CF$_3$—Ph | Me | H | 0 | m.p.: 205-208° C. |
| 1-16 | SO$_2$Et | 4-CF$_3$ | 2-CF$_3$—Ph | Me | H | 0 | m.p.: 124-125° C. |
| 1-17 | SO$_2$Et | 4-CF$_3$ | 3-CF$_3$—Ph | Me | H | 0 | m.p.: 165-166° C. |
| 1-18 | SOEt | 4-CF$_3$ | 4-CF$_3$—Ph | Me | H | 0 | m.p.: 154-155° C. |
| 1-19 | SEt | 4-CF$_3$ | 4-Cl—Ph | Me | H | 0 | m.p.: 92-94° C. |
| 1-20 | SO$_2$Et | 4-CF$_3$ | 4-Cl—Ph | Me | H | 0 | m.p.: 172-173° C. |
| 1-21 | SEt | 4-CF$_3$ | 4-$^t$Bu—Ph | Me | H | 0 | m.p.: 117-118° C. |
| 1-22 | SO$_2$Et | 4-CF$_3$ | 4-$^t$Bu—Ph | Me | H | 0 | m.p.: 201-202° C. |
| 1-23 | SEt | 4-CF$_3$ | 4-CF$_3$—Ph | Et | H | 0 | viscous oil |
| 1-24 | SO$_2$Et | 4-CF$_3$ | 4-CF$_3$—Ph | Et | H | 0 | m.p.: 109-110° C. |
| 1-25 | SEt | 4-CF$_3$ | 4-CF$_3$—Ph | Me | Cl | 0 | m.p.: 140-142° C. |
| 1-26 | SEt | 4-$^t$Bu | 4-CF$_3$—Ph | Me | H | 1 | m.p.: 200° C. up |
| 1-27 | SEt | 4-$^t$Bu | 4-CF$_3$—Ph | Me | H | 0 | m.p.: 127-129° C. |
| 1-28 | SEt | 4-CF$_3$ | 4-CF$_3$—Ph | Me | Br | 0 | m.p.: 140-141° C. |
| 1-29 | SO$_2$Et | 4-CF$_3$ | 4-CF$_3$—Ph | Me | Br | 0 | m.p.: 153-154° C. |
| 1-30 | SO$_2$Et | 4-$^t$Bu | 4-CF$_3$—Ph | Me | H | 0 | m.p.: 197-199° C. |
| 1-31 | OEt | 4-CF$_3$ | 4-CF$_3$—Ph | Me | H | 0 | m.p.: 98-101° C. |
| 1-32 | SEt | 3-CF$_3$ | 4-CF$_3$—Ph | Me | H | 0 | viscous oil |
| 1-33 | SO$_2$Et | 3-CF$_3$ | 4-CF$_3$—Ph | Me | H | 0 | amorphous |
| 1-34 | SOEt | 3-CF$_3$ | 4-CF$_3$—Ph | Me | H | 0 | m.p.: 183-184° C. |
| 1-35 | SO$_2$Et | 4-CF$_3$ | 4-OCF$_3$—Ph | Me | H | 0 | m.p.: 140-142° C. |
| 1-36 | SO$_2$Et | 4-CF$_3$ | 3,5-Cl$_2$—Ph | Me | H | 0 | m.p.: 130-131° C. |
| 1-37 | SO$_2$Et | 4-CF$_3$ | 3,5-F$_2$—Ph | Me | H | 0 | m.p.: 127-131° C. |
| 1-38 | SO$_2$Et | 4-CF$_3$ | 3,5-(CF$_3$)$_2$—Ph | Me | H | 0 | m.p.: 158-162° C. |
| 1-39 | SO$_2$Et | 4-CF$_3$ | 3,4-Cl$_2$—Ph | Me | H | 0 | m.p.: 150-151° C. |
| 1-40 | SO$_2$Et | 4-CF$_3$ | 2,6-Cl$_2$—Ph | Me | H | 0 | m.p.: 160-162° C. |
| 1-41 | SO$_2$Et | 4-CF$_3$ | 3-Cl—Ph | Me | H | 0 | m.p.: 127-134° C. |
| 1-42 | SO$_2$Et | 4-CF$_3$ | 4-F—Ph | Me | H | 0 | m.p.: 154-156° C. |
| 1-43 | SO$_2$Et | 4-CF$_3$ | Ph | Me | H | 0 | m.p.: 149-152° C. |
| 1-44 | SO$_2$Et | 4-CF$_3$ | 4-OMe—Ph | Me | H | 0 | m.p.: 170-171° C. |
| 1-45 | SO$_2$Et | 4-CF$_3$ | 4-Me—Ph | Me | H | 0 | m.p.: 180-181° C. |
| 1-46 | SO$_2$Et | 4-CF$_3$ | 6-CF$_3$-pyridine-3-yl | Me | H | 0 | m.p.: 165-167° C. |
| 1-47 | SO$_2$Et | 4-CF$_3$ | 5-CF$_3$-pyridine-3-yl | Me | H | 0 | m.p.: 126-129° C. |
| 1-48 | SO$_2$Et | 4-CF$_3$ | 6-CF$_3$-pyridine-2-yl | Me | H | 0 | m.p.: 141-142° C. |
| 1-49 | SO$_2$Et | 4-CF$_3$ | 2-Cl-pyridine-4-yl | Me | H | 0 | m.p.: 162-164° C. |
| 1-50 | SO$_2$Et | 4-CF$_3$ | 4-CF$_3$—Ph | Me | Cl | 0 | m.p.: 82-85° C. |
| 1-51 | SO$_2$Et | 4-CF$_3$ | 4-CF$_3$—Ph | $^c$Pr | H | 0 | amorphous |
| 1-52 | SO$_2$Et | 4-CF$_3$ | 4-NO$_2$—Ph | Me | H | 0 | m.p.: 170-172° C. |
| 1-53 | SO$_2$Et | 4-CF$_3$ | 4-NH$_2$—Ph | Me | H | 0 | m.p.: 208-210° C. |
| 1-54 | SO$_2$Et | 4-CF$_3$ | 4-Br—Ph | Me | H | 0 | m.p.: 192-195° C. |
| 1-55 | SO$_2$Et | 4-CF$_3$ | 4-Br—Ph | Me | Br | 0 | m.p.: 182-184° C. |
| 1-56 | SO$_2$Et | 4-CF$_3$ | 3-Cl-5-CF$_3$-pyridine-2-yl | Me | H | 0 | m.p.: 128-129° C. |
| 1-57 | SO$_2$Et | 4-CF$_3$ | 4-CHF$_2$O—Ph | Me | H | 0 | m.p.: 149-151° C. |

TABLE 1-continued

| No. | R¹ | (X¹)n | Ar | R² | R³ | m | Physical Property |
|---|---|---|---|---|---|---|---|
| 1-58 | SO$_2$Et | 4-CF$_3$ | 4-CF$_3$-pyridine-2-yl | Me | H | 0 | m.p.: 164-169° C. |
| 1-59 | SO$_2$Et | 4-CF$_3$ | 4-CF$_3$-6-(4-CF$_3$-pyridine-2-yl)pyridine-2-yl | Me | H | 0 | m.p.: 206-209° C. |
| 1-60 | SO$_2$Et | 4-F | 4-CF$_3$—Ph | Me | H | 0 | m.p.: 171-172° C. |
| 1-61 | SEt | 2-CF$_3$ | 4-CF$_3$—Ph | Me | H | 0 | viscous oil |
| 1-62 | SO$_2$Et | 2-CF$_3$ | 4-CF$_3$—Ph | Me | H | 0 | viscous oil |
| 1-63 | SOEt | 2-CF$_3$ | 4-CF$_3$—Ph | Me | H | 0 | amorphous |
| 1-64 | SEt | 4-CF$_3$ | 1-CF$_3$—1H-pyrazol-4-yl | Me | H | 0 | m.p.: 120-121° C. |
| 1-65 | SO$_2$Et | 4-CF$_3$ | 1-CF$_3$—1H-pyrazol-4-yl | Me | H | 0 | m.p.: 177-179° C. |
| 1-66 | SO$_2$Et | 4-CF$_3$ | 2-F-4-CF$_3$—Ph | Me | H | 0 | m.p.: 121-126° C. |
| 1-67 | SO$_2$Et | 4-CF$_3$ | 2-SEt-4-CF$_3$—Ph | Me | H | 0 | m.p.: 171-172° C. |
| 1-68 | SO$_2$Et | 4-CF$_3$ | 2-SO$_2$Et-4-CF$_3$—Ph | Me | H | 0 | m.p.: 154-156° C. |
| 1-69 | SO$_2$Et | 4-CF$_3$ | 2-CN-4-CF$_3$—Ph | Me | H | 0 | m.p.: 142-144° C. |
| 1-70 | SEt | 3-CF$_3$ | 4-CF$_3$—Ph | Me | H | 0 | m.p.: 134-136° C. |
| 1-71 | SOEt | 3-CF$_3$ | 4-CF$_3$—Ph | Me | H | 0 | m.p.: 165-168° C. |
| 1-72 | SO$_2$Et | 3-CF$_3$ | 4-CF$_3$—Ph | Me | H | 0 | m.p.: 200° C. up |
| 1-73 | SO$_2$Et | 4-CF$_3$ | 4-CF$_3$—Ph | CF$_3$ | H | 0 | m.p.: 155-156° C. |
| 1-74 | SO$_2$Et | 4-CF$_3$ | 4-CF$_3$—Ph | C($^2$H)$_3$ | H | 0 | m.p.: 138-141° C. |
| 1-75 | SEt | 4-CF$_3$ | 2-Cl-4-CF$_3$—Ph | Me | H | 0 | m.p.: 126-128° C. |
| 1-76 | SO$_2$Et | 4-CF$_3$ | 2-Cl-4-CF$_3$—Ph | Me | H | 0 | n$_D$(19.0° C.)1.5309 |
| 1-77 | SO$_2$Et | 4-CF$_3$ | 4-(perfluoropropan-2-yl)Ph | Me | H | 0 | m.p.: 214-217° C. |
| 1-78 | SEt | 4-CF$_3$ | 4-C$_2$F$_5$—Ph | Me | H | 0 | m.p.: 99-101° C. |
| 1-79 | SO$_2$Et | 4-CF$_3$ | 4-C$_2$F$_5$—Ph | Me | H | 0 | m.p.: 155-157° C. |
| 1-80 | SEt | 4-CF$_3$ | 4-(1,1,1,3,3,3-F$_6$-2-OMe-propan-2-yl)Ph | Me | H | 0 | n$_D$(19.8° C.)1.525 |
| 1-81 | SO$_2$Et | 4-CF$_3$ | 4-(1,1,1,3,3,3-F$_6$-2-OMe-propan-2-yl)Ph | Me | H | 0 | m.p.: 183-185° C. |
| 1-82 | SO$_2$Et | 4-CF$_3$ | 4-CF$_3$—Ph | CHF$_2$ | H | 0 | m.p.: 133-135° C. |
| 1-83 | SO$_2$Et | 4-CF$_3$ | 4-SCF$_3$—Ph | Me | H | 0 | m.p.: 140-143° C. |
| 1-84 | SO$_2$Et | 4-CF$_3$ | 4-SOCF$_3$—Ph | Me | H | 0 | m.p.: 120-122° C. |
| 1-85 | SO$_2$Et | 4-CF$_3$ | 6-Cl-pyridine-3-yl | Me | H | 0 | m.p.: 168-170° C. |
| 1-86 | SO$_2$Et | 4-CF$_3$ | 2-CF$_3$-pyrimidin-5-yl | Me | H | 0 | m.p.: 170-174° C. |
| 1-87 | SO$_2$Me | 4-CF$_3$ | 4-CF$_3$—Ph | Me | H | 0 | viscous oil |
| 1-88 | SO$_2$Et | 4-CF$_3$ | 4-SO$_2$CF$_3$—Ph | Me | H | 0 | m.p.: 132-134° C. |
| 1-89 | SO$_2$Et | 4-CF$_3$ | 2,2-F$_2$-benzo[1,3]dioxol-5-yl | Me | H | 0 | m.p.: 106-108° C. |
| 1-90 | SO$_2$Et | 4-CF$_3$ | 4-(1,1,1,3,3,3-F$_6$-propan-2-yl)Ph | Me | H | 0 | m.p.: 194-196° C. |
| 1-91 | SO$_2$Et | 4-CF$_3$ | 4-CF$_3$CH$_2$—Ph | Me | H | 0 | m.p.: 154-156° C. |
| 1-92 | SO$_2$Et | 4-CF$_3$ | 6-OCF$_3$-pyridine-3-yl | Me | H | 0 | viscous oil |
| 1-93 | SO$_2$Et | 4-CF$_3$ | 4-I—Ph | Me | H | 0 | m.p.: 233-235° C. |
| 1-94 | SO$_2$Et | 4-CF$_3$ | 4-OCH$_2$OMe—Ph | Me | H | 0 | m.p.: 129-130° C. |
| 1-95 | SO$_2$Et | 4-CF$_3$ | 4-OSO$_2$CF$_3$—Ph | Me | H | 0 | m.p.: 155-156° C. |
| 1-96 | SO$_2$Et | 4-CF$_3$ | 4-OCH$_2$CF$_3$—Ph | Me | H | 0 | m.p.: 159-160° C. |
| 1-97 | SO$_2$Et | 4-CF$_3$ | 4-SF$_5$—Ph | Me | H | 0 | m.p.: 160-163° C. |
| 1-98 | SO$_2$Et | 4-CF$_3$ | 3-Cl-4-CF$_3$—Ph | Me | H | 0 | m.p.: 124-126° C. |
| 1-99 | SO$_2$Et | 4-CF$_3$ | 6-C$_2$F$_5$-pyridine-3-yl | Me | H | 0 | amorphous |
| 1-100 | SO$_2$Et | 4-CF$_3$ | 4-CN—Ph | Me | H | 0 | m.p.: 184-188° C. |
| 1-101 | SO$_2$Et | 4-CF$_3$ | 3-F-4-CF$_3$—Ph | Me | H | 0 | m.p.: 85-88° C. |
| 1-102 | SO$_2$Et | 4-CF$_3$ | 3-CN-4-CF$_3$—Ph | Me | H | 0 | m.p.: 171-173° C. |
| 1-103 | OCH$_2$OMe | 4-CF$_3$ | 4-CF$_3$—Ph | Me | H | 0 | m.p.: 102-103° C. |
| 1-104 | OH | 4-CF$_3$ | 4-CF$_3$—Ph | Me | H | 0 | m.p.: 217-221° C. |
| 1-105 | OCH$_2$SMe | 4-CF$_3$ | 4-CF$_3$—Ph | Me | H | 0 | m.p.: 136-138° C. |
| 1-106 | OCH$_2$SOMe | 4-CF$_3$ | 4-CF$_3$—Ph | Me | H | 0 | m.p.: 160-163° C. |
| 1-107 | OCH$_2$SO$_2$Me | 4-CF$_3$ | 4-CF$_3$—Ph | Me | H | 0 | viscous oil |
| 1-108 | OCH$_2$CF$_3$ | 4-CF$_3$ | 4-CF$_3$—Ph | Me | H | 0 | n$_D$(18.6° C.)1.5098 |
| 1-109 | OSO$_2$Me | 4-CF$_3$ | 4-CF$_3$—Ph | Me | H | 0 | n$_D$(19.4° C.)1.5360 |
| 1-110 | SO$_2$Et | 4-CF$_3$ | 6-CF$_3$-pyridazin-3-yl | Me | H | 0 | m.p.: 222-224° C. |
| 1-111 | SO$_2$Et | 4-CF$_3$ | 2-F-4-OCF$_3$—Ph | Me | H | 0 | m.p.: 116-119° C. |
| 1-112 | SEt | 4-CF$_3$ | 4-OCF$_3$—Ph | Me | H | 0 | m.p.: 115-116° C. |
| 1-113 | SOEt | 4-CF$_3$ | 4-OCF$_3$—Ph | Me | H | 0 | m.p.: 153-155° C. |
| 1-114 | SO$_2$Et | 4-CF$_3$ | 3-CF$_3$-4-Cl—Ph | Me | H | 0 | m.p.: 104-109° C. |
| 1-115 | SO$_2$Et | 4-CF$_3$ | 3-CF$_3$-4-Cl—Ph | Me | 3-CF$_3$-4-Cl-Ph | 0 | m.p.: 206-209° C. |
| 1-116 | SO$_2$Et | 4-CF$_3$ | 4-(4-CF$_3$—Ph)Ph | Me | H | 0 | m.p.: 224-226° C. |
| 1-117 | SO$_2$Et | 4-CF$_3$ | thiophen-2-yl | Me | I | 0 | m.p.: 233-234° C. |
| 1-118 | SO$_2$Et | 4-CF$_3$ | thiophen-2-yl | Me | H | 0 | m.p.: 178-179° C. |
| 1-119 | SO$_2$Et | 4-CF$_3$ | 4-SC$_2$F$_5$—Ph | Me | H | 0 | m.p.: 93-95° C. |
| 1-120 | SO$_2$Et | 4-CF$_3$ | 6-((4-OMe—Ph)CH$_2$O)-pyridine-3-yl | Me | H | 0 | amorphous |
| 1-121 | SO$_2$Et | 4-CF$_3$ | 6-Br-pyridine-3-yl | Me | H | 0 | m.p.: 198-201° C. |
| 1-122 | SO$_2$Et | 4-CF$_3$ | 7-F-quinolin-3-yl | Me | H | 0 | m.p.: 196-200° C. |
| 1-123 | SO$_2$Et | 4-CF$_3$ | 4-OCF$_2$CHF$_2$—Ph | Me | H | 0 | m.p.: 138-141° C. |
| 1-124 | SO$_2$Et | 4-CF$_3$ | 2,6-Cl$_2$-4-CF$_3$ | Me | H | 0 | m.p.: 180-182° C. |
| 1-125 | SO$_2$Et | 4-CF$_3$ | 2,6-Me$_2$-4-(perfluoropropan-2-yl)Ph | Me | H | 0 | viscous oil |

TABLE 2 shows the substituents of the compound represented by formula (2).

[Chemical formula 16]

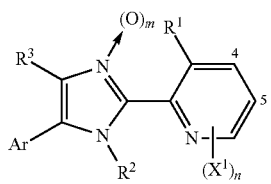
(2)

TABLE 2

| No. | $R^1$ | $(X^1)n1$ | Ar | $R^2$ | $R^3$ | m | Physical Property |
|---|---|---|---|---|---|---|---|
| 2-1 | SO$_2$Et | 5-CF$_3$ | 4-CF$_3$—Ph | Me | H | 0 | m.p.: 97-101° C. |
| 2-2 | SEt | 5-CF$_3$ | 4-CF$_3$—Ph | Me | H | 0 | m.p.: 151-153° C. |
| 2-3 | F | — | 4-CF$_3$—Ph | Me | H | 0 | m.p.: 213-214° C. |
| 2-4 | SEt | — | 4-CF$_3$—Ph | Me | H | 0 | m.p.: 145-147° C. |
| 2-5 | SO$_2$Et | — | 4-CF$_3$—Ph | Me | H | 0 | m.p.: 133-136° C. |
| 2-6 | SO$_2$Et | — | 4-OCF$_3$—Ph | Me | H | 0 | $n_D$(22.1° C.)1.5629 |
| 2-7 | SO$_2$Et | — | 6-CF$_3$-pyridine-3-yl | Me | H | 0 | m.p.: 157-163° C. |
| 2-8 | SO$_2$Et | — | 4-C$_2$F$_5$—Ph | Me | H | 0 | m.p.: 145-147° C. |
| 2-9 | SO$_2$Et | — | 4-SCF$_3$—Ph | Me | H | 0 | m.p.: 135-137° C. |

TABLE 3 shows the substituents of the compounds represented by formula (3).

[Chemical formula 17]

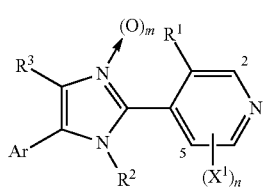
(3)

TABLE 3

| No. | $R^1$ | $(X^1)n1$ | Ar | $R^2$ | $R^3$ | m | Physical Property |
|---|---|---|---|---|---|---|---|
| 3-1 | SO$_2$Et | — | 4-CF$_3$—Ph | Me | H | 0 | nD(21.0° C.)1.5452 |
| 3-2 | SEt | — | 4-CF$_3$—Ph | Me | H | 0 | nD(21.4° C.)1.6008 |
| 3-3 | F | — | 4-CF$_3$—Ph | Me | H | 1 | m.p. 189-193° C. |
| 3-4 | F | — | 4-CF$_3$—Ph | Me | H | 0 | m.p. 153-155° C. |

TABLE 4 shows the substitutents of the compound represented by formula (4).

[Chemical formula 18]

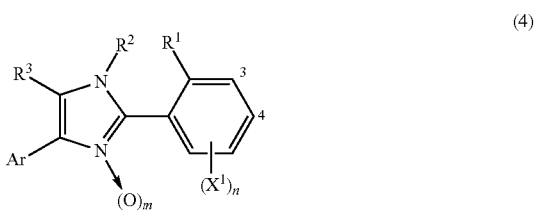
(4)

TABLE 4

| No. | $R^1$ | $(X^1)n$ | Ar | $R^2$ | $R^3$ | m | Physical Property |
|---|---|---|---|---|---|---|---|
| 4-1 | SEt | 4-CF$_3$ | 4-CF$_3$—Ph | OMe | H | 0 | m.p.: 106-109° C. |
| 4-2 | SEt | 4-CF$_3$ | 4-CF$_3$—Ph | OH | H | 0 | m.p.: 245-249° C. |
| 4-3 | SO$_2$Et | 4-CF$_3$ | 4-CF$_3$—Ph | Me | Me | 0 | m.p.: 195-197° C. |
| 4-4 | SEt | 4-CF$_3$ | 4-CF$_3$—Ph | Me | Me | 0 | m.p.: 147-149° C. |
| 4-5 | SEt | 4-CF$_3$ | 4-CF$_3$—Ph | Me | Br | 0 | m.p.: 153-155° C. |
| 4-6 | SEt | 4-CF$_3$ | 4-CF$_3$—Ph | Me | H | 0 | m.p.: 109-111° C. |
| 4-7 | F | 4-CF$_3$ | 4-CF$_3$—Ph | Me | H | 0 | m.p.: 73-75° C. |
| 4-8 | SO$_2$Et | 4-CF$_3$ | 4-CF$_3$—Ph | Me | H | 0 | m.p.: 180-181° C. |
| 4-9 | SOEt | 4-CF$_3$ | 4-CF$_3$—Ph | Me | H | 0 | m.p.: 138-139° C. |

TABLE 5 shows the substituents of the compounds represented by formula (5).

[Chemical formula 19]

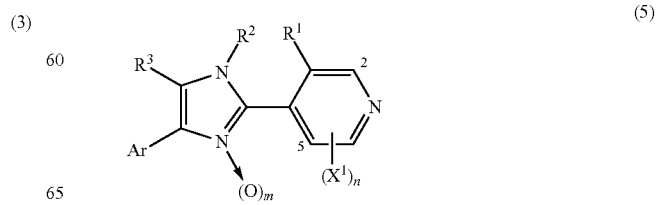
(5)

TABLE 5

| No. | R¹ | (X¹)n1 | Ar | R² | R³ | m | Physical Property |
|---|---|---|---|---|---|---|---|
| 5-1 | SEt | — | 4-CF$_3$—Ph | Me | H | 0 | m.p. 79-84° C. |

[Chemical formula 20]

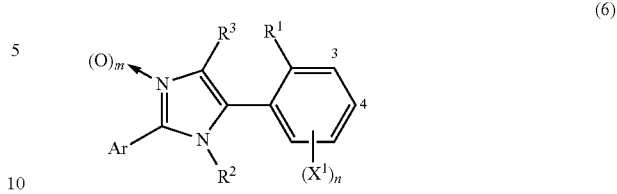

(6)

TABLE 6 shows the substituents of the compounds represented by formula (6).

TABLE 6

| No. | R¹ | (X¹)n1 | Ar | R² | R³ | m | Physical Property |
|---|---|---|---|---|---|---|---|
| 6-1 | SO$_2$Et | 4-CF$_3$ | 4-CF$_3$—Ph | Me | H | 0 | n$_D$(22.0° C.)1.529 |
| 6-2 | F | 4-CF$_3$ | 4-CF$_3$—Ph | Me | H | 0 | m.p.: 144-145° C. |
| 6-3 | SEt | 4-CF$_3$ | 4-CF$_3$—Ph | Me | H | 0 | m.p.: 118-121° C. |
| 6-4 | SO$_2$Et | 4-CF$_3$ | 2-F-4-CF$_3$—Ph | Me | H | 0 | m.p.: 140-141° C. |
| 6-5 | SEt | 4-CF$_3$ | 4-OCF$_3$—Ph | Me | H | 0 | m.p.: 92-94° C. |
| 6-6 | SO$_2$Et | 4-CF$_3$ | 4-OCF$_3$—Ph | Me | H | 0 | viscous oil |
| 6-7 | SO$_2$Et | 4-CF$_3$ | 4-OCF$_3$—Ph | Me | Cl | 0 | m.p.: 140-142° C. |
| 6-8 | SEt | 4-CF$_3$ | 6-CF$_3$-pyridine-3-yl | Me | H | 0 | m.p.: 138-139° C. |
| 6-9 | SOEt | 4-CF$_3$ | 6-CF$_3$-pyridine-3-yl | Me | H | 0 | m.p.: 170-172° C. |
| 6-10 | SO$_2$Et | 4-CF$_3$ | 6-CF$_3$-pyridine-3-yl | Me | H | 0 | n$_D$(20.1° C.)1.5334 |
| 6-11 | SO$_2$Et | 4-CF$_3$ | 4-C$_2$F$_5$—Ph | Me | H | 0 | n$_D$(18.3° C.)1.5183 |
| 6-12 | SO$_2$Et | 4-OCF$_3$ | 4-CF$_3$—Ph | Me | H | 0 | viscous oil |
| 6-13 | SO$_2$Et | 4-SO$_2$Et | 4-CF$_3$—Ph | Me | H | 0 | viscous oil |
| 6-14 | SO$_2$Et | 4-Cl | 4-CF$_3$—Ph | Me | H | 0 | viscous oil |
| 6-15 | S$^i$Pr | 4-CF$_3$ | 4-CF$_3$—Ph | Me | H | 0 | m.p.: 114-116° C. |
| 6-16 | SO$_2^i$Pr | 4-CF$_3$ | 4-CF$_3$—Ph | Me | H | 0 | n$_D$(20.0° C.)1.5258 |
| 6-17 | SO$_2$Et | 4-CN | 4-CF$_3$—Ph | Me | H | 0 | m.p.: 192-193° C. |
| 6-18 | SO$_2$Et | 4-CF$_3$ | 4-SCF$_3$—Ph | Me | H | 0 | viscous oil |
| 6-19 | SO$_2$Et | 4-CF$_3$ | 2-CF$_3$-thiazol-5-yl | Me | H | 0 | viscous oil |
| 6-20 | F | 4-CO$_2$Me | 4-CF$_3$—Ph | Me | H | 0 | m.p.: 188-189° C. |
| 6-21 | SEt | 4-CONMe$_2$ | 4-CF$_3$—Ph | Me | H | 0 | m.p.: 116-117° C. |
| 6-22 | SO$_2$Et | 4-CONMe$_2$ | 4-CF$_3$—Ph | Me | H | 0 | m.p.: 170-173° C. |
| 6-23 | SO$_2$Et | 4-Me | 4-CF$_3$—Ph | Me | H | 0 | m.p.: 172-175° C. |
| 6-24 | SO$_2$Et | 4-CO$_2$Me | 4-CF$_3$—Ph | Me | H | 0 | amorphous |
| 6-25 | SO$_2$Et | 4-CO$_2^t$Bu | 4-CF$_3$—Ph | Me | H | 0 | viscous oil |
| 6-26 | SO$_2$Et | 4-CH$_2$OH | 4-CF$_3$—Ph | Me | H | 0 | m.p.: 184-188° C. |
| 6-27 | SO$_2$Et | 4-CHO | 4-CF$_3$—Ph | Me | H | 0 | amorphous |
| 6-28 | SO$_2$Et | 4-CHF$_2$ | 4-CF$_3$—Ph | Me | H | 0 | amorphous |
| 6-29 | SO$_2$Et | 4-CF$_3$ | 4-CF$_3$—Ph | Me | Cl | 0 | amorphous |
| 6-30 | SO$_2$Et | 4-CF$_3$ | 4-CF$_3$—Ph | Me | H | 0 | m.p.: 110-115° C. |
| 6-31 | SO$_2$Et | 4-CF$_3$ | 4-CF$_3$—Ph | Me | Br | 0 | m.p.: 210-212° C. |
| 6-32 | SO$_2$Et | 4-CF$_3$ | 4-CF$_3$—Ph | Me | Me | 0 | m.p.: 157-160° C. |
| 6-33 | Cl | 2-Cl-4-CF$_3$ | 4-CF$_3$—Ph | Me | H | 0 | m.p.: 139-141° C. |
| 6-34 | SEt | 2-Cl-4-CF$_3$ | 4-CF$_3$—Ph | Me | H | 0 | viscous oil |
| 6-35 | SO$_2$Et | 2-Cl-4-CF$_3$ | 4-CF$_3$—Ph | Me | H | 0 | viscous oil |
| 6-36 | SO$_2$Et | 4-CF$_3$ | 5-CF$_3$-thiophen-2-yl | Me | H | 0 | m.p.: 158-159° C. |
| 6-37 | CN | 4-CF$_3$ | 4-CF$_3$—Ph | Me | H | 0 | m.p.: 175-179° C. |
| 6-38 | CONMe$_2$ | 4-CF$_3$ | 4-CF$_3$—Ph | Me | H | 0 | n$_D$(22.1° C.)1.5407 |
| 6-39 | CONHMe | 4-CF$_3$ | 4-CF$_3$—Ph | Me | H | 0 | m.p.: 190-193° C. |
| 6-40 | SEt | 4-CF$_3$ | 3-CF$_3$—Ph | Me | H | 0 | m.p.: 127-129° C. |
| 6-41 | SO$_2$Et | 4-CF$_3$ | 3-CF$_3$—Ph | Me | H | 0 | m.p.: 86-88° C. |
| 6-42 | SMe | 4-CF$_3$ | 4-CF$_3$—Ph | Me | H | 0 | m.p.: 115-117° C. |
| 6-43 | SOMe | 4-CF$_3$ | 4-CF$_3$—Ph | Me | H | 0 | m.p.: 157-159° C. |
| 6-44 | SO$_2$Me | 4-CF$_3$ | 4-CF$_3$—Ph | Me | H | 0 | viscous oil |
| 6-45 | SCH$_2$CF$_3$ | 4-CF$_3$ | 4-CF$_3$—Ph | Me | H | 0 | m.p.: 107-110° C. |
| 6-46 | SO$_2$CH$_2$CF$_3$ | 4-CF$_3$ | 4-CF$_3$—Ph | Me | H | 0 | m.p.: 142-143° C. |
| 6-47 | N=S(=O)Me$_2$ | 4-CF$_3$ | 4-CF$_3$—Ph | Me | H | 0 | m.p.: 154-156° C. |
| 6-48 | CONH$^s$Bu | 4-CF$_3$ | 4-CF$_3$—Ph | Me | H | 0 | m.p.: 85-87° C. |
| 6-49 | CON(Me)$^s$Bu | 4-CF$_3$ | 4-CF$_3$—Ph | Me | H | 0 | n$_D$(21.8° C.)1.5288 |
| 6-50 | SEt | 4-CF$_3$ | 4-SF$_5$—Ph | Me | H | 0 | m.p.: 103-105° C. |
| 6-51 | SO$_2$Et | 4-CF$_3$ | 4-SF$_5$—Ph | Me | H | 0 | n$_D$(22.8° C.)1.5238 |
| 6-52 | SEt | 4-CF$_3$ | 4-Cl—Ph | Me | H | 0 | m.p.: 112-114° C. |
| 6-53 | SO$_2$Et | 4-CF$_3$ | 4-Cl—Ph | Me | H | 0 | amorphous |
| 6-54 | SEt | 4-CF$_3$ | 3-Cl-4-CF$_3$—Ph | Me | H | 0 | viscous oil |
| 6-55 | SO$_2$Et | 4-CF$_3$ | 3-Cl-4-CF$_3$—Ph | Me | H | 0 | amorphous |
| 6-56 | SO$_2$Et | 4-CF$_3$ | 4-C$_2$F$_5$—Ph | Me | H | 0 | amorphous |
| 6-57 | SEt | 4-CF$_3$ | 2,2-F$_2$-benzo[1,3]dioxol-5-yl | Me | H | 0 | n$_D$(23.2° C.)1.5659 |
| 6-58 | SO$_2$Et | 4-CF$_3$ | 2,2-F$_2$-benzo[1,3]dioxol-5-yl | Me | H | 0 | m.p.: 140-144° C. |
| 6-59 | S$^n$Pr | 4-CF$_3$ | 4-CF$_3$—Ph | Me | H | 0 | m.p.: 104-106° C. |

TABLE 6-continued

| No. | $R^1$ | $(X^1)n1$ | Ar | $R^2$ | $R^3$ | m | Physical Property |
|---|---|---|---|---|---|---|---|
| 6-60 | $SO_2^nPr$ | 4-$CF_3$ | 4-$CF_3$—Ph | Me | H | 0 | m.p.: 126-130° C. |
| 6-61 | S(=O)(=N—CN)Et | 4-$CF_3$ | 4-$CF_3$—Ph | Me | H | 0 | amorphous |
| 6-62 | F | 4-$CF_3$ | 5-$CF_3$-pyridine-2-yl | Me | H | 0 | m.p.: 111-113° C. |
| 6-63 | SEt | 4-$CF_3$ | 5-$CF_3$-pyridine-2-yl | Me | H | 0 | m.p.: 105-107° C. |
| 6-64 | $SO_2Et$ | 4-$CF_3$ | 5-$CF_3$-pyridine-2-yl | Me | H | 0 | amorphous |
| 6-65 | S(=O)(=N—COCF$_3$)Et | 4-$CF_3$ | 4-$CF_3$—Ph | Me | H | 0 | viscous oil |
| 6-66 | S(=O)(=NH)Et | 4-$CF_3$ | 4-$CF_3$—Ph | Me | H | 0 | m.p.: 138-140° C. |
| 6-67 | S(=O)(=NMe)Et | 4-$CF_3$ | 4-$CF_3$—Ph | Me | H | 0 | m.p.: 168-169° C. |
| 6-68 | SEt | 4-$CF_3$ | 3,5-$(CF_3)_2$—Ph | Me | 3,5-$(CF_3)_2$—Ph | 0 | viscous oil |
| 6-69 | $SO_2Et$ | 4-$CF_3$ | 3,5-$(CF_3)_2$—Ph | Me | H | 0 | viscous oil |
| 6-70 | SEt | 4-$CF_3$ | 4-(perfluoropropan-2-yl)Ph | Me | Br | 0 | m.p.: 105-107° C. |
| 6-71 | SOEt | 4-$CF_3$ | 4-(perfluoropropan-2-yl)Ph | Me | H | 0 | m.p.: 170-171° C. |
| 6-72 | SEt | 4-$CF_3$ | 3,4-$Cl_2$—Ph | Me | Br | 0 | m.p.: 119-120° C. |
| 6-73 | SEt | 4-$CF_3$ | 3,4-$Cl_2$—Ph | Me | H | 0 | viscous oil |
| 6-74 | $SO_2Et$ | 4-$CF_3$ | 3,4-$Cl_2$—Ph | Me | H | 0 | m.p.: 125-126° C. |
| 6-75 | F | 4-$CF_3$ | 4-CN—Ph | Me | H | 0 | m.p.: 177-178° C. |
| 6-76 | SEt | 4-$CF_3$ | 6-$C_2F_5$-pyridine-3-yl | Me | Br | 0 | viscous oil |
| 6-77 | SEt | 4-$CF_3$ | 4-CN—Ph | Me | H | 0 | m.p.: 130-132° C. |
| 6-78 | F | 4-$CF_3$ | 3-SEt-4-$CF_3$—Ph | Me | H | 0 | m.p.: 160-163° C. |
| 6-79 | F | 4-$CF_3$ | 3-SOEt-4-$CF_3$—Ph | Me | H | 0 | m.p.: 130-133° C. |
| 6-80 | F | 4-$CF_3$ | 3-$SO_2Et$-4-$CF_3$—Ph | Me | H | 0 | m.p.: 141-143° C. |
| 6-81 | SEt | 4-$CF_3$ | 3-SEt-4-$CF_3$—Ph | Me | H | 0 | m.p.: 89-90° C. |
| 6-82 | $SO_2Et$ | 4-$CF_3$ | 3-SOEt-4-$CF_3$—Ph | Me | H | 0 | m.p.: 90-94° C. |
| 6-83 | $SO_2Et$ | 4-$CF_3$ | 3-$SO_2Et$-4-$CF_3$—Ph | Me | H | 0 | m.p.: 177-180° C. |
| 6-84 | F | 4-$CF_3$ | 3-$NO_2$-4-$CF_3$—Ph | Me | H | 0 | m.p.: 99-102° C. |
| 6-85 | $CH_2CONHMe$ | 4-$CF_3$ | 4-$CF_3$—Ph | Me | H | 0 | m.p.: 150-152° C. |
| 6-86 | $CH_2CONMe_2$ | 4-$CF_3$ | 4-$CF_3$—Ph | Me | H | 0 | viscous oil |
| 6-87 | F | 4-$CF_3$ | 3-$NH_2$-4-$CF_3$—Ph | Me | H | 0 | m.p.: 158-159° C. |
| 6-88 | SEt | 4-$CF_3$ | 3-$NH_2$-4-$CF_3$—Ph | Me | H | 0 | m.p.: 130-132° C. |
| 6-89 | $SO_2Et$ | 4-$CF_3$ | 3-$NH_2$-4-$CF_3$—Ph | Me | H | 0 | m.p.: 200-202° C. |
| 6-90 | SEt | 4-$CF_3$ | 3-Br-4-$CF_3$—Ph | Me | H | 0 | m.p.: 116-118° C. |
| 6-91 | $SO_2Et$ | 4-$CF_3$ | 3-Br-4-$CF_3$—Ph | Me | H | 0 | amorphous |
| 6-92 | SEt | 4-$CF_3$ | 4-$^nBt$-6-$C_2F_5$-pyridine-3-yl | Me | H | 0 | m.p.: 110-112° C. |
| 6-93 | SEt | 4-$CF_3$ | 3-Cl-4-$OCF_3$—Ph | Me | Br | 0 | m.p.: 104-105° C. |
| 6-94 | SEt | 4-$CF_3$ | 3-Cl-4-$OCF_3$—Ph | Me | H | 0 | viscous oil |
| 6-95 | SOEt | 4-$CF_3$ | 3-Cl-4-$OCF_3$—Ph | Me | H | 0 | amorphous |
| 6-96 | SEt | 4-$CF_3$ | 2-Cl-4-$CF_3$—Ph | Me | Br | 0 | m.p.: 128-129° C. |
| 6-97 | $SO_2Et$ | 4-$CF_3$ | 4-CN—Ph | Me | H | 0 | m.p.: 183-185° C. |
| 6-98 | $SO_2Et$ | 4-$CF_3$ | 4-CHO | Me | H | 0 | m.p.: 147-148° C. |

TABLE 7 shows the substituents of the compounds represented by formula (7).

[Chemical 21]

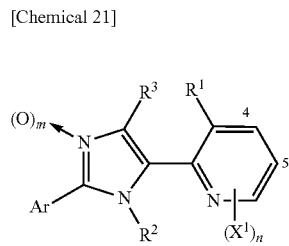

(7)

TABLE 7

| No. | $R^1$ | $(X^1)n1$ | Ar | $R^2$ | $R^3$ | m | Physical Property |
|---|---|---|---|---|---|---|---|
| 7-1 | SEt | 5-$CF_3$ | 4-$CF_3$—Ph | Me | H | 0 | m.p. 123-125° C. |
| 7-2 | $SO_2Et$ | 5-$CF_3$ | 4-$CF_3$—Ph | Me | H | 0 | m.p. 172-173° C. |

TABLE 8 shows the substituents of the compounds represented by formula (8).

[Chemical formula 22]

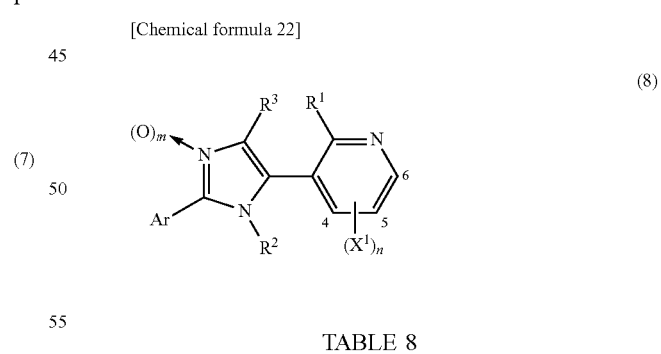

(8)

TABLE 8

| No. | $R^1$ | $(X^1)n1$ | Ar | $R^2$ | $R^3$ | m | Physical Property |
|---|---|---|---|---|---|---|---|
| 8-1 | SEt | 6-$CF_3$ | 4-$CF_3$—Ph | Me | H | 0 | viscous oil |
| 8-2 | $SO_2Et$ | 6-$CF_3$ | 4-$CF_3$—Ph | Me | H | 0 | m.p. 216-218° C. |

TABLE 9 shows the substituents of the compounds represented by formula (9).

[Chemical formula 23]

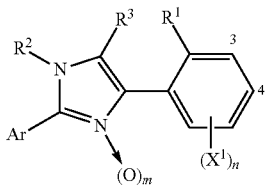

TABLE 9

| | No. | R¹ | (X¹)n1 | Ar | R² | R³ | m | Physical Property |
|---|---|---|---|---|---|---|---|---|
| (9) | 9-1 | F | 4-CF₃ | 4-CF₃—Ph | Me | H | 0 | m.p.: 153-154° C. |
| | 9-2 | SEt | 4-CF₃ | 4-CF₃—Ph | Me | H | 0 | m.p.: 93-94° C. |
| | 9-3 | SO₂Et | 4-CF₃ | 4-CF₃—Ph | Me | H | 0 | m.p.: 138-140° C. |

TABLE 10 shows ¹H-NMR data measured for some compounds selected from TABLE 1 to TABLE 9. The measuring temperature is 23° C. (*: measuring temperature of 140° C.).

TABLE 10

| Compound No. | NMR データ (δ ppm) |
|---|---|
| 1-2 | ¹H-NMR (400 MHz, CDCl₃): 8.88 (m, 1H), 7.94 (m, 1H), 7.77 (d, 1H), 7.71 (s, 1H), 7.61 (s, 1H), 7.52 (m, 1H), 3.86 (s, 3H), 2.94 (q, 2H), 1.30 (t, 3H). |
| 1-9 | ¹H-NMR (400 MHz, CDCl₃): d 7.84 (d, 1H), 7.67-7.50 (m, 6H), 7.46 (d, 1H), 7.18 (s, 1H), 3.21 (s, 3H), 2.88 (q, 2H), 1.29 (t, 3H). |
| 1-10 | ¹H-NMR (400 MHz, CDCl₃): d 7.78 (d, 2H), 7.61-7.50 (m, 5H), 7.43 (s, 1H), 7.40 (m, 1H), 3.47 (s, 1H), 3.00-2.88 (m, 1H), 1.29 (t, 3H). |
| 1-23 | ¹H-NMR (400 MHz, CDCl₃): d 7.73 (d, 2H), 7.61-7.59 (m, 3H), 7.54-7.50 (m, 2H), 7.28 (s, 1H), 3.94 (q, 2H), 2.65 (q, 2H), 1.32 (t, 3H), 0.97 (t, 3H). |
| 1-33 | ¹H-NMR (400 MHz, CDCl₃): d 7.73 (d, 2H), 7.68-7.66 (m, 2H), 7.60 (d, 2H), 7.46 (d, 1H), 7.33 (s, 1H), 3.52 (s, 3H), 2.97 (q, 2H), 1.34 (t, 3H). |
| 1-34 | H-NMR (400 MHz, CDCl₃): d 8.34 (d, 1H), 7.99 (dd, 1H), 7.85 (d, 1H), 7.74 (d, 2H), 7.60 (d, 2H), 7.26 (s, 1H), 3.48-3.42 (m, 5H), 1.26 (m, 3H). |
| 1-51 | ¹H-NMR (400 MHz, CDCl₃): d 8.48 (d, 1H), 8.01 (dd, 1H), 7.80 (d, 1H), 7.71 (m, 4H), 7.23 (s, 1H), 3.70 (q, 2H), 3.40 (m, 1H), 1.31 (t, 3H), 0.64 (m, 4H). |
| 1-61 | ¹H-NMR (400 MHz, CDCl₃): d 7.72 (d, 2H), 7.61-7.60 (m, 3H), 7.57-7.55 (m, 2H), 7.36 (s, 1H), 3.39 (s, 3H), 2.98-2.88 (m, 2H), 1.30 (t, 3H). |
| 1-62 | ¹H-NMR (400 MHz, CDCl₃): d 8.43 (d, 1H), 8.13 (d, 1H), 7.89 (t, 1H), 7.72 (d, 2H), 7.60 (d, 2H), 7.30 (s, 1H), 3.48-3.22 (m, 2H), 3.37 (s, 3H), 1.21 (t, 3H). |
| 1-63 | ¹H-NMR (400 MHz, CDCl₃): d 8.30 (d, 1H), 7.98 (m, 1H), 7.91 (t, 1H), 7.75 (d, 2H), 7.59 (d, 2H), 7.27 (s, 1H), 3.41 (s, 3H), 3.23-2.82 (m, 2H), 1.26 (t, 3H). |
| 1-87 | ¹H-NMR (400 MHz, CDCl₃): d 8.52 (d, 1H), 8.04 (dd, 1H), 7.75-7.73 (m, 3H), 7.60 (d, 2H), 7.28 (s, 1H), 3.44 (s, 3H), 3.30 (s, 3H). |
| 1-92 | ¹H-NMR (400 MHz, CDCl₃): d 8.46-8.45 (m, 2H), 8.04 (m, 1H), 7.90 (m, 1H), 7.73 (d, 1H), 7.14 (d, 1H), 3.46 (q, 2H), 3.42 (s, 3H), 1.26 (t, 3H). |
| 1-99 | ¹H-NMR (400 MHz, CDCl₃): d 8.90 (d, 1H), 8.47 (d, 1H), 8.05 (dd, 1H), 8.00 (dd, 1H), 7.83 (d, 1H), 7.75 (d, 1H), 3.48 (s, 3H), 3.46 (q, 2H), 1.27 (t, 3H). |
| 1-107 | ¹H-NMR (400 MHz, CDCl₃): d 7.76-7.74 (m, 3H), 7.64-7.61 (m, 2H), 7.56 (d, 1H), 7.34 (m, 1H), 7.31 (s, 1H), 4.96 (s, 2H), 3.59 (s, 3H), 2.76 (s, 3H). |
| 1-120 | ¹H-NMR (400 MHz, CDCl₃): d 8.44 (d, 1H), 8.00 (dd, 1H), 7.66 (d, 1H), 7.40-7.36 (m, 2H), 7.32 (m, 2H), 7.05 (s, 1H), 6.90 (m, 2H), 6.69 (d, 1H), 5.13 (s, 2H), 3.80 (s, 3H), 3.43 (q, 2H), 3.27 (s, 3H), 1.24 (t, 3H). |
| 1-125 | ¹H-NMR (400 MHz, CDCl₃): d 8.47 (d, 1H), 8.02 (dd, 1H), 7.73 (d, 1H), 7.39 (s, 2H), 7.03 (s, 1H), 3.47 (q, 2H), 3.09 (s, 3H), 1.26 (t, 3H). |
| 6-6 | ¹H-NMR (400 MHz, CDCl₃): d 8.51 (d, 1H), 8.01 (dd, 1H), 7.76-7.73 (m, 2H), 7.67 (d, 2H), 7.35 (m, 1H), 7.15 (s, 1H), 3.48 (s, 3H), 3.07 (q, 2H), 1.20 (t, 3H). |
| 6-12 | ¹H-NMR (400 MHz, CDCl₃): d 8.10 (d, 1H), 7.84 (d, 2H), 7.75 (d, 2H), 7.58 (m, 2H), 7.14 (s, 1H), 3.50 (s, 3H), 3.07 (q, 2H), 1.20 (t, 3H). |
| 6-13 | ¹H-NMR (400 MHz, CDCl₃): d 8.74 (d, 1H), 8.29 (dd, 1H), 7.85 (d, 2H), 7.78-7.73 (m, 3H), 7.20 (s, 1H), 3.51 (s, 3H), 3.26 (q, 2H), 3.08 (q, 2H), 1.39 (t, 3H), 1.22 (t, 3H). |
| 6-14 | ¹H-NMR (400 MHz, CDCl₃): d 8.23 (d, 1H), 8.84 (d, 2H), 7.75 (d, 2H), 7.72 (dd, 1H), 7.45 (d, 1H), 7.36 (s, 1H), 7.13 (s, 1H), 3.48 (s, 3H), 3.05 (q, 2H), 1.20 (t, 3H). |
| 6-18 | ¹H-NMR (400 MHz, CDCl₃): d 8.49 (m, 1H), 8.00 (m, 1H), 7.75 (m, 4H), 7.64 (m, 1H), 7.15 (s, 1H), 3.49 (s, 3H), 3.05 (q, 2H), 1.19 (t, 3H). |
| 6-19 | ¹H-NMR (400 MHz, CDCl₃): d 8.50 (d, 1H), 8.19 (d, 2H), 8.03 (dd, 1H), 7.65 (d, 1H), 7.17 (s, 1H), 7.13 (s, 1H), 3.61 (s, 3H), 3.05 (q, 2H), 1.22 (t, 3H). |
| 6-24 | ¹H-NMR (400 MHz, CDCl₃): d 8.86 (d, 1H), 8.40 (dd, 1H), 7.85 (d, 2H), 7.75 (d, 2H), 7.61 (d, 1H), 7.27 (s, 1H), 4.02 (s, 3H), 3.49 (s, 3H), 3.07 (q, 2H), 1.20 (t, 3H). |
| 6-25 | ¹H-NMR (400 MHz, CDCl₃): d 8.78 (d, 1H), 8.33 (dd, 1H), 7.85 (m, 2H), 7.75 (m, 2H), 7.57 (d, 1H), 7.16 (s, 1H), 3.48 (s, 3H), 3.06 (q, 2H), 1.65 (s, 9H), 1.20 (t, 3H). |
| 6-27 | ¹H-NMR (400 MHz, CDCl₃): d 10.20 (s, 1H), 8.72 (d, 1H), 8.26 (dd, 1H), 7.85 (m, 2H), 7.76 (m, 2H), 7.70 (d, 1H), 7.19 (s, 1H), 3.51 (s, 3H), 3.08 (q, 2H), 1.21 (t, 3H). |
| 6-28 | ¹H-NMR (400 MHz, CDCl₃): d 8.38 (s, 1H), 7.92 (d, 1H), 7.85 (d, 2H), 7.76 (d, 2H), 7.63 (d, 1H), 7.17 (s, 1H), 6.81 (t, 1H), 3.50 (s, 3H), 3.07 (q, 2H), 1.20 (t, 3H). |
| 6-29 | ¹H-NMR (400 MHz, CDCl₃): d 8.52 (d, 1H), 8.06 (dd, 1H), 7.84 (m, 2H), 7.76 (m, 2H), 7.68 (d, 1H), 3.50 (s, 3H), 3.10 (q, 2H), 1.23 (t, 3H). |
| 6-34 | ¹H-NMR (400 MHz, CDCl₃): d 7.88 (d, 2H), 7.75 (d, 2H), 7.54 (s, 1H), 7.38 (s, 1H), 7.19 (s, 1H), 3.50 (s, 3H), 2.95 (q, 2H), 1.35 (t, 3H). |
| 6-35 | ¹H-NMR (400 MHz, CDCl₃): d 8.42 (d, 1H), 8.09 (d, 1H), 7.86 (d, 2H), 7.77 (d, 2H), 7.16 (s, 1H), 3.50 (s, 3H), 3.19 (q, 2H), 1.28 (t, 3H). |
| 6-44 | ¹H-NMR (400 MHz, CDCl₃): d 8.58 (d, 1H), 8.02 (dd, 1H), 7.85 (d, 2H), 7.76 (d, 2H), 7.68 (d, 1H), 7.22 (s, 1H), 3.50 (s, 3H), 3.02 (q, 2H). |

TABLE 10-continued

| Compound No. | NMR データ (δ ppm) |
|---|---|
| 6-53 | $^1$H-NMR (400 MHz, CDCl$_3$): d 8.50 (m, 1H), 7.99 (m, 1H), 7.67-7.64 (m, 3H), 7.48 (d, 1H), 7.14 (s, 1H), 3.46 (s, 3H), 3.07 (q, 2H), 1.20 (t, 3H). |
| 6-54 | $^1$H-NMR (400 MHz, CDCl$_3$): d 7.93 (s, 1H), 7.81 (d, 1H), 7.74 (m, 1H), 7.56 (s, 1H), 7.48 (m, 1H), 7.40 (d, 1H), 7.21 (s, 1H), 3.57 (s, 3H), 2.96 (t, 2H), 1.34 (t, 3H). |
| 6-55 | $^1$H-NMR (400 MHz, CDCl$_3$): d 8.51 (m, 1H), 8.01 (m, 1H), 7.91 (s, 1H), 7.81 (d, 1H), 7.71 (m, 1H), 7.66 (d, 1H), 7.18 (s, 1H), 3.51 (s, 3H), 3.07 (q, 2H), 1.21 (t, 3H). |
| 6-56 | $^1$H-NMR (400 MHz, CDCl$_3$): d 8.51 (m, 1H), 8.01 (m, 1H), 7.78 (m, 4H), 7.66 (d, 1H), 7.17 (s, 1H), 3.51 (s, 3H), 3.07 (q, 2H), 1.21 (t, 3H). |
| 6-61 | $^1$H-NMR (400 MHz, CDCl$_3$): d 8.53 (br s, 1H), 8.13 (dd, 1H), 7.86-7.76 (m, 5H), 7.12 (s, 1H), 3.56 (br s, 3H), 3.45 (m, 2H), 3.07 (q, 2H), 1.38 (br t, 3H). |
| 6-64 | $^1$H-NMR (400 MHz, CDCl$_3$): d 8.88 (m, 1H), 8.51 (m, 1H), 8.39 (d, 1H), 8.02 (m, 2H), 7.65 (d, 1H), 7.21 (s, 1H), 3.89 (s, 3H), 3.08 (q, 2H), 1.22 (t, 3H). |
| 6-65 | $^1$H-NMR (400 MHz, DMSO-d6)*: d 8.38 (s, 1H), 8.27 (d, 1H), 7.96-7.83 (m, 5H), 7.33 (s, 1H), 3.80 (m, 2H), 3.48 (s, 3H), 1.28 (t, 3H). |
| 6-68 | $^1$H-NMR (400 MHz, CDCl$_3$): d 8.26 (s, 2H), 8.00 (s, 1H), 7.90 (s, 2H), 7.65 (d, 2H), 7.54 (m, 1H), 7.41 (d, 1H), 3.54 (s, 3H), 3.07-2.93 (m, 2H), 1.32 (t, 3H). |
| 6-69 | $^1$H-NMR (400 MHz, CDCl$_3$): d 8.51 (d, 1H), 8.19 (s, 2H), 8.02 (dd, 1H), 7.96 (s, 1H), 7.67 (d, 1H), 7.20 (s, 1H), 3.53 (s, 3H), 3.09 (q, 2H), 1.23 (t, 3H). |
| 6-73 | $^1$H-NMR (400 MHz, CDCl$_3$): d 7.85 (d, 1H), 7.57-7.55 (m, 3H), 7.48 (dd, 1H), 7.39 (d, 1H), 7.18 (s, 1H), 3.53 (s, 3H), 2.95 (q, 2H), 1.34 (t, 3H). |
| 6-76 | $^1$H-NMR (400 MHz, CDCl$_3$): d 9.09 (d, 1H), 8.32 (dd, 1H), 7.85 (dd, 1H), 7.62 (s, 1H), 7.55 (dd, 1H), 7.45 (d, 1H), 3.59 (s, 3H), 2.97 (q, 2H), 1.33 (t, 3H). |
| 6-86 | $^1$H-NMR (400 MHz, CDCl$_3$): d 7.83 (d, 2H), 7.75 (d, 2H), 7.65-7.63 (m, 2H), 7.12 (s, 1H), 3.75 (s, 2H), 3.53 (s, 3H), 2.94 (s, 3H), 2.87 (s, 3H). |
| 6-91 | $^1$H-NMR (400 MHz, CDCl$_3$): d 8.51 (s, 1H), 8.12 (s, 1H), 8.01 (d, 1H), 7.81 (d, 1H), 7.76 (d, 1H), 7.66 (d, 1H), 7.20 (s, 1H), 3.51 (s, 3H), 3.07 (q, 2H), 1.21 (t, 3H). |
| 6-94 | $^1$H-NMR (400 MHz, CDCl$_3$): d 7.88 (d, 1H), 7.67 (dd, 1H), 7.53 (s, 1H), 7.49-7.39 (m, 3H), 7.18 (s, 1H), 3.54 (s, 3H), 2.95 (q, 2H), 1.34 (t, 3H). |
| 6-97 | $^1$H-NMR (400 MHz, CDCl$_3$): d 8.51 (d, 1H), 8.01 (dd, 1H), 7.84 (d, 1H), 7.67-7.63 (m, 2H), 7.45 (m, 1H), 7.15 (s, 1H), 3.49 (s, 3H), 3.07 (q, 2H), 1.21 (t, 3H). |
| 8-1 | $^1$H-NMR (400 MHz, CDCl$_3$): d 7.86 (d, 2H), 7.76 (d, 2H), 7.63 (d, 1H), 7.45 (d, 1H), 7.26 (s, 1H), 3.58 (s, 3H), 3.23 (q, 2H), 1.37 (t, 3H). |

[Biological Examination]

The following test examples demonstrate that the diarylimidazole compound of the present invention (hereinafter, may be referred to as "the compound of the present invention") is useful as an active ingredient of harmful organisms control agent, especially as an active ingredient of insecticide. In addition, the term "part" is based on weight.

(Preparation of Emulsion for Test)

5 parts of the compound of the present invention, 93.6 parts of dimethyl formamide and 1.4 parts of polyoxyethylene alkylaryl ether were mixed and dissolved to obtain emulsion (I) including 5% of active ingredient.

Test Example 1 Efficacy Test Against *Pseudaletia Separate*

Emulsion (I) was diluted with water so that the concentration of the compound of the present invention reaches 125 ppm. Maize leaves were soaked in the diluted liquid for 30 seconds. Then the maize leaves were put on Petri dishes, followed by inoculating 5 second-instar larvae of *Pseudaletia separate*. The Petri dishes were placed in a temperature-controlled room with a temperature of 25° C. and humidity of 60%. Mortality was investigated after 6 days were passed, and the insect mortality rate was calculated. The test was repeated twice.

Efficacy test against *Pseudaletia separate* was carried out for the compounds shown in TABLE 11. All of the compounds demonstrated 80% or more of insect mortality rate against *Pseudaletia separate*.

TABLE 11

| Compound No. | | | | | | |
|---|---|---|---|---|---|---|
| 1-1 | 1-35 | 1-64 | 1-85 | 1-111 | 3-2 | 6-32 |
| 1-2 | 1-36 | 1-65 | 1-86 | 1-112 | 3-1 | 6-35 |
| 1-3 | 1-38 | 1-66 | 1-87 | 1-113 | 6-1 | 6-36 |
| 1-7 | 1-39 | 1-67 | 1-88 | 1-114 | 6-3 | 6-37 |
| 1-11 | 1-42 | 1-69 | 1-89 | 1-119 | 6-4 | 6-41 |
| 1-14 | 1-46 | 1-71 | 1-90 | 1-121 | 6-7 | 6-43 |
| 1-15 | 1-47 | 1-74 | 1-91 | 1-122 | 6-10 | 6-51 |
| 1-17 | 1-48 | 1-75 | 1-92 | 1-123 | 6-11 | 6-52 |
| 1-18 | 1-52 | 1-76 | 1-93 | 2-1 | 6-12 | 6-53 |
| 1-19 | 1-54 | 1-77 | 1-97 | 2-2 | 6-13 | 6-54 |
| 1-20 | 1-56 | 1-78 | 1-98 | 2-4 | 6-14 | 6-55 |
| 1-23 | 1-57 | 1-79 | 1-99 | 2-5 | 6-18 | 6-56 |
| 1-24 | 1-58 | 1-81 | 1-100 | 2-6 | 6-19 | 6-57 |
| 1-32 | 1-60 | 1-82 | 1-101 | 2-7 | 6-24 | 6-58 |
| 1-33 | 1-62 | 1-83 | 1-102 | 2-8 | 6-28 | 6-63 |
| 1-34 | 1-63 | 1-84 | 1-110 | 2-9 | 6-31 | 6-64 |

Test Example 2 Efficacy Test Against *Spodoptera Litura*

Emulation (I) was diluted with water so that the concentration of the compound of the present invention reaches 125 ppm. Cabbage leaves were soaked in the diluted liquid for 30 seconds. Then the cabbage leaves were put on Petri dishes, followed by inoculating 5 second-instar larvae of *Spodoptera litura*. The Petri dishes were placed in a temperature-controlled room with a temperature was 25° C. and humidity of 60%. Mortality was investigated after 6 days were passed, and the insect mortality rate was calculated. The test was repeated twice.

Efficacy test against *Spodoptera litura* was carried out for the compounds shown in TABLE 12. All of the compounds demonstrated 80% or more of insect mortality rate against *Spodoptera litura*.

TABLE 12

| Compound No. | | | | | | |
|---|---|---|---|---|---|---|
| 1-1 | 1-33 | 1-58 | 1-90 | 1-111 | 6-11 | 6-56 |
| 1-2 | 1-35 | 1-69 | 1-91 | 1-112 | 6-18 | 6-57 |
| 1-3 | 1-36 | 1-74 | 1-92 | 1-113 | 6-32 | 6-58 |
| 1-7 | 1-38 | 1-77 | 1-97 | 1-114 | 6-35 | 6-63 |
| 1-15 | 1-39 | 1-79 | 1-98 | 1-119 | 6-36 | 6-64 |
| 1-17 | 1-42 | 1-83 | 1-99 | 1-121 | 6-51 | |
| 1-18 | 1-46 | 1-85 | 1-100 | 1-122 | 6-52 | |
| 1-19 | 1-47 | 1-87 | 1-101 | 2-1 | 6-53 | |
| 1-20 | 1-54 | 1-88 | 1-102 | 6-1 | 6-54 | |
| 1-24 | 1-57 | 1-89 | 1-110 | 6-6 | 6-55 | |

Test Example 3 Efficacy Test Against *Plutella xylostella*

Emulsion (I) was diluted with water so that the concentration of the compound of the present invention reaches 125 ppm. Cabbage leaves were soaked in the diluted liquid for 30 seconds. Then the cabbage leaves were put on Petri dishes, followed by inoculating 5 second-instar larvae of *Plutella xylostella*. The Petri dishes were placed in a temperature-controlled room with a temperature was 25° C. and humidity of 60%. Mortality was investigated after 3 days were passed, and the insect mortality rate was calculated. The test was repeated twice.

Efficacy test against *Plutella xylostella* was carried out for the compounds shown in TABLE 13. All of the compounds demonstrated 80% or more of mortality rate against *Plutella xylostella*.

TABLE 13

| Compound No. | | | | | | |
|---|---|---|---|---|---|---|
| 1-1 | 1-17 | 1-35 | 1-46 | 1-77 | 2-5 | 6-11 |
| 1-2 | 1-18 | 1-36 | 1-47 | 1-79 | 3-2 | |
| 1-3 | 1-20 | 1-38 | 1-54 | 1-90 | 3-1 | |
| 1-7 | 1-24 | 1-39 | 1-57 | 2-1 | 6-1 | |
| 1-15 | 1-33 | 1-42 | 1-58 | 2-2 | 6-6 | |

Test Example 4 Efficacy Test Against *Aphis gossypii*

Cucumber plants were raised in No. 3 pots and the first true leaves were inoculated with nymphs of *Aphis gossypii*. Emulation (I) was diluted with water so that the concentration of the compound of the present invention reaches 125 ppm, followed by spraying the diluted liquid on the cucumber seedlings. The cucumber seedlings were then placed in a temperature-controlled room with a temperature of 25° C. and humidity of 60%. Mortality was investigated after 4 days were passed from the spraying, and the insect mortality rate of *Aphis gossypii* was calculated. The test was repeated twice.

Efficacy test against *Aphis gossypii* was carried out for the compounds shown in TABLE 14. All of the compounds demonstrated 80% or more of mortality rate against *Aphis gossypii*.

TABLE 14

| Compound No. | | | | | | |
|---|---|---|---|---|---|---|
| 1-3 | 1-35 | 1-65 | 1-88 | 1-100 | 3-1 | 6-24 |
| 1-8 | 1-39 | 1-66 | 1-89 | 1-101 | 5-1 | 6-28 |
| 1-13 | 1-42 | 1-69 | 1-90 | 1-102 | 6-1 | 6-36 |
| 1-14 | 1-46 | 1-79 | 1-91 | 1-111 | 6-6 | 6-41 |
| 1-17 | 1-47 | 1-83 | 1-92 | 1-114 | 6-12 | 6-51 |
| 1-20 | 1-54 | 1-84 | 1-97 | 2-1 | 6-14 | 6-52 |
| 1-24 | 1-57 | 1-86 | 1-98 | 2-5 | 6-18 | 6-53 |
| 1-33 | 1-58 | 1-87 | 1-99 | 3-2 | 6-19 | 6-55 |

Test Example 5 Efficacy Test Against *Bemisia tabaci*

Emulsion (I) was diluted with water so that the concentration of the compound of the present invention reaches 125 ppm, then the diluted liquid was sprayed on young seedlings of tomato, followed by air drying. On the day of the spraying, B-type adult *Bemisia tabaci* were released to the seedlings so as to lay eggs. The number of parasitic larvae was calculated after 12 days were passed from the spraying. The efficacy of the compound was evaluated by the following equation of prevention rate. The test was repeated twice.

Prevention rate=[1−(Nt)/(Nc)]×100

Nt: number of parasites in spray-treatment area
Nc: number of parasites in control area Efficacy test against *Bemisia tabaci* was carried out for the compounds shown in TABLE 15. All of the compounds demonstrated 80% or more of prevention rate against *Bemisia tabaci*.

TABLE 15

| Compound No. | | | | |
|---|---|---|---|---|
| 1-3 | 1-66 | 1-86 | 1-92 | 3-2 |
| 1-35 | 1-79 | 1-87 | 1-98 | 3-1 |
| 1-65 | 1-83 | 1-91 | 2-1 | 6-1 |

Test Example 6 Efficacy Test Against *Tetranychus kanzawai*

Kidney bean plants were raised in No. 3 pots and the primary leaves were inoculated with 10 adult female *Tetranychus kanzawai*. Emulation (I) was diluted with water so that the concentration of the compound of the present invention reaches 125 ppm, followed by spraying the diluted liquid on the kidney bean seedlings. The kidney bean seedlings were then placed in a temperature-controlled room with a temperature of 25° C. and humidity of 65%. Mortality of the adult *Tetranychus kanzawai* was investigated after 10 days were passed from the spraying, and the insect mortality rate of *Tetranychus kanzawai* was calculated. The test was repeated twice.

The efficacy test against *Tetranychus kanzawai* was carried out for the compounds shown in TABLE 16. All of the compounds demonstrated 90% or more of mortality rate against *Tetranychus kanzawai*.

TABLE 16

| Compound No. | | | | | |
|---|---|---|---|---|---|
| 1-4 | 1-31 | 1-60 | 1-109 | 6-10 | 9-1 |
| 1-9 | 1-41 | 1-61 | 3-4 | 6-25 | |
| 1-25 | 1-46 | 1-103 | 6-9 | 6-62 | |

Test Example 7 Efficacy Test Against *Aphis gossypii* (Root-Dipping Test)

Cucumber plants raised in No. 3 pots were pulled out from the pots, then the soil attached to the roots was washed with tap water, followed by hydroponic-cultivating the cucumber plants by soaking the roots in tap water. The cucumber seedlings were inoculated with nymphs of *Aphis gossypii*. Emulsion (I) was diluted with water to obtain a diluted liquid with a concentration of 8 ppm of the compound of the present invention. The tap water was replaced with the diluted liquid, and then the hydrophonic-cultivation was continued in a temperature-controlled room with a temperature was 25° C. and humidity of 60%.

After 6 days were passed from the hydrophonic-cultivation in the diluted liquid, mortality of *Aphis gossypii* was investigated and the insect mortality rate was calculated. The test was repeated twice.

The efficacy test against *Aphis gossypii* was carried out for Compound 3-1, and the insect mortality rate of Compound 3-1 was 80% or more.

Test Example 8 Efficacy Test Against *Musca Domestica*

The compound of the present invention was diluted with acetone, followed by dropping to 1 g of cube sugar so that the concentration reaches to 100 ppm. The cube sugar was placed in a plastic cup and 10 adult female *Musca domestica* were released therein, followed by putting the lid on the cup. The cup was kept at 25° C., the mortality was investigated after 24 hours was passed from the releasing of *Musca domestica* and the insect mortality rate was calculated by the following equation. The test was repeated twice.

Insect mortality rate (%)=(number of dead insects/ number of sample insects)×100

The efficacy test against *Musca domestica* was carried out for Compound 1-35. As a result, the insect mortality rate against the adult female *Musca domestica* was 100%.

Test Example 9 Efficacy Test Against *Culex pipiens*

Emulsion (I) was diluted with water so that the concentration of the compound of the present invention reaches 2 ppm to prepare a chemical solution for test. 20 first-instar larvae of *Culex pipiens* were released into 100 ml of the chemical solution for test, then the number of dead insects was calculated after 1 day was passed, and the insect mortality rate was calculated by the following equation. The test was repeated twice.

Insect mortality rate (%)=(number of dead insects/ number of sample insects)×100

The efficacy test against the first-instar larvae of *Culex pipiens* was carried out for Compound 1-35. As a result, the insect mortality rate against the first-instar larvae of *Culex pipiens* was 100%.

Test Example 10 Efficacy Test Against *Plutella xylostella* (Soil Irrigating Test)

Emulsion (I) was diluted with water so that the concentration of the compound of the present invention reaches 500 ppm to prepare a chemical solution for test. 10 ml of the chemical solution for test was irrigated to the plant feet of bok choy seedlings (extending period of 7 major leaves) raised in No. 3 pots, followed by keeping them in a warm room with a temperature of 25° C. for 7 days. The bok choy seedlings were placed in a glass warm room and 300 adult *Plutella xylostella* were released to 50 bok choy seedlings. After 7 days were passed from releasing the insects, the number of living larvae of *Plutella xylostella* parasitic in the bok choy seedlings was investigated and the prevention rate was calculated by the following equation. The test was repeated twice.

Prevention rate=[1−(Nt)/(Nc)]×100

Nt: number of parasites in spray-treatment area
Nc: number of parasites in control area The efficacy test against *Plutella xylostella* was carried out for Compounds 1-46, 1-47, 1-65, 1-69, 1-85, 1-102, 1-121, 2-5, 3-1, 6-28 and 6-53. As a result, all of the compounds demonstrated 80% or more of prevention rate against *Plutella xylostella*.

Test Example 11 Efficacy Test Against *Pseudaletia separate* (Seed Treatment Test)

0.1 g of each compound of the present invention was diluted with 2 ml of acetone to prepare a chemical solutions for test. 10 g of wheat seeds was added to the chemical solution for test and air dried, followed by seedling 100 seeds in a planter. After keeping the planter in a warm room with a temperature of 25° C. for 7 days, 100 first-instar larvae of *Pseudaletia* separate were released in the planter. The planter was kept in a war room with a temperature of 25° C., the number of living *Pseudaletia* separate was investigated after 3 days were passed, and the prevention rate was calculated by the following equation. The test was repeated twice.

Prevention rate=[1−(Nt)/(Nc)]×100

Nt: number of parasites in spray-treatment area
Nc: number of parasites in control area The efficacy test against the first-instar larvae of *Pseudaletia* separate was carried out for Compounds 1-47, 1-65, 1-69, 1-102, 2-5 and 6-53. As a result, all of the compounds demonstrated 80% or more of prevention rate against the first-instar larvae of *Pseudaletia* separate.

Test Example 12 Efficacy Test Against *Rhopalosiphum padi* (Seed Treatment Test)

0.1 g of each compound of the present invention was diluted with 2 ml of acetone to prepare chemical solutions for test. 10 g of wheat seeds was added to the chemical solution for test and air dried, followed by seedling 100 seeds in a planter. After keeping the planter in a warm room with a temperature of 25° C. for 7 days, 50 adult *Rhopalosiphum padi* were released in the planter. The number of living *Rhopalosiphum padi* was investigated after 6 days were passed, and the prevention rate was calculated by the following equation. The test was repeated twice.

Prevention rate=[1−(Nt)/(Nc)]×100

Nt: number of parasites in spray-treatment area
Ne: number of parasites in control area The efficacy test against *Rhopalosiphum padi* was carried out for Compounds 1-47, 1-65, 1-69, 1-102, 2-5 and 6-53. As a result, all of the compounds demonstrated 80% or more of prevention rate against *Rhopalosiphum padi*.

INDUSTRIAL APPLICABILITY

The diarylimidazole compound or salt thereof according to the present invention can prevent harmful organisms which are harmful for agricultural crops and cause the problem of hygiene. Particularly, the compound or salt thereof can effectively prevent *acarus* and insecticides. Furthermore, the compound or salt thereof can prevent external parasites and internal parasite which are handful for humans and animals and thereby useful for industry.

The invention claimed is:

1. A compound represented by formula II or salt thereof,

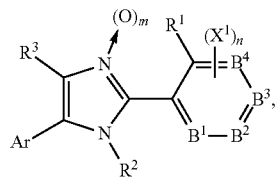

(II)

in formula (II), $B^1$, $B^2$, $B^3$ and $B^4$ each independently represents a carbon atom, $X^1$ represents an unsubstituted or substituted C1-6 alkyl group, unsubstituted or substituted C2-6 alkenyl group, unsubstituted or substituted C2-6 alkynyl group, hydroxy group, unsubstituted or substituted C1-6 alkoxy group, formyl group, unsubstituted or substituted C1-6 alkyl carbonyl group, unsubstituted or substituted C1-6 alkoxycarbonyl group, unsubstituted or substituted C1-6 alkyl aminocarbonyl group, mercapto group, unsubstituted or substituted C1-6 alkyl thio group, unsubstituted or substituted C1-6 alkyl sulfinyl group, unsubstituted or substituted C1-6 alkyl sulfonyl group, unsubstituted or substituted C3-8 cycloalkyl group, unsubstituted or substituted C6-10 aryl group, unsubstituted or substituted amino group, halogeno group, cyano group, or nitro group, n represents a chemically acceptable number of $X^1$ and represents an integer of 0 to 4, when n is 2 or more, $X^1$s may be the same or different, and when n is 2 or more, two $X^1$s may bond together to form a ring, $R^1$ represents a halogeno group, hydroxy group, cyano group, substituted C1-6 alkyl group, unsubstituted or substituted C1-6 alkoxy group, unsubstituted or substituted C1-6 alkyl thio group, unsubstituted or substituted C1-6 alkyl sulfinyl group, unsubstituted or substituted C1-6 alkyl sulfonyl group, unsubstituted or substituted C1-6 alkyl sulfonyloxy group, C1-6 alkyl aminocarbonyl group, C1-6 alkyl sulfoximino group or a group represented by —S(=O)(=N—$R^a$)—$R^b$, in the formula, $R^a$ represents a hydrogen atom, cyano group, C1-6 alkyl group or unsubstituted or substituted C1-6 alkyl carbonyl group, $R^b$ represents a C1-6 alkyl group, $R^2$ represents an unsubstituted or substituted C1-6 alkyl group, unsubstituted or substituted C2-6 alkenyl group, unsubstituted or substituted C2-6 alkynyl group, unsubstituted or substituted C3-8 cycloalkyl group, hydroxy group, unsubstituted or substituted, C1-6 alkoxy group, formyl group, unsubstituted or substituted C1-6 alkyl carbonyl group, unsubstituted or substituted C1-6 alkoxycarbonyl group, or unsubstituted or substituted C1-6 alkyl sulfonyl group, $R^2$ is a substituent bonding with any one of the two nitrogen atoms on the imidazole ring, m represents a number of the oxide group bonding with the nitrogen atom which does not bond with $R^2$ on the imidazole ring, and represents 0 or 1, $R^3$ represents a hydrogen atom, unsubstituted or substituted C1-6 alkyl group, unsubstituted or substituted C6-10 aryl group, halogeno group, cyano group or nitro group, Ar represents an unsubstituted or substituted C6-10 aryl group, the substituent is a C1-6 alkyl group, a C2-6 alkenyl group, a C2-6 alkynyl group, a C3-8 cycloalkyl group, a C6-10 aryl group, a C6-10 aryl C1-6 alkyl group, a hydroxy group, a C1-6 alkoxy group, a C2-6 alkenyloxy group, a C2-6 alkynyloxy group, a C6-10 aryloxy group, a C6-10 aryl C1-6 alkoxy group, a formyl group, a C1-6 alkyl carbonyl group, formyloxy group, a C1-6 alkyl carbonyloxy group, a C6-10 aryl carbonyl group, a C1-6 alkoxycarbonyl group, a C1-6 alkoxycarbonyloxy group, a carboxyl group, a halogeno group, a C1-6 haloalkyl group, a C2-6 haloalkenyl group, a C2-6 haloalkynyl group, a C1-6 haloalkoxy group, a C2-6 haloalkenyloxy group, a C1-6 haloalkyl carbonyl group, an amino group, a C1-6 alkyl substituted amino group, a C6-10 aryl amino group, a C6-10 aryl C1-6 alkyl amino group, a formyl amino group, a C1-6 alkyl carbonyl amino group, a C1-6 alkoxycarbonyl amino group, an unsubstituted or substituted aminocarbonyl group, an imino C1-6 alkyl group, as unsubstituted or substituted N-hydroxyimino C1-6 alkyl group, an aminocarbonyloxy group a C1-6 alkyl substituted aminocarbonyloxy group, a mercapto group, a C1-6 alkyl thio group, a C1-6 haloalkyl thio group, a C6-10 aryl thio group, a C1-6 alkyl sulfinyl group, a C1-6 haloalkyl sulfinyl group, a C6-10 aryl sulfinyl group, a C1-6 alkyl sulfonyl group, a C1-6 haloalkyl sulfonyl group, a C6-10 aryl sulfonyl group, an alkyl sulfonyloxy group, a haloalkyl sulfonyloxy group, a tri C1-6 alkyl substituted silyl group, a tri C6-10 aryl substituted silyl group, a cyano group or a nitro group.

2. A harmful organism control agent comprising as an active ingredient at least one selected from the group consisting of the compound and salt thereof defined in claim 1, and a carrier.

* * * * *